United States Patent [19]

Bey et al.

[11] 4,439,619

[45] Mar. 27, 1984

[54] FLUORINATED PENTENE DIAMINE DERIVATIVES

[75] Inventors: Philippe Bey, Strasbourg, France; Fritz Gerhart, Kehl-Leutesheim, Fed. Rep. of Germany; Michel Jung, Illkirch-Graffenstaden, France

[73] Assignee: Merrell Toraude et Compagnie, Strasbourg, France

[21] Appl. No.: 295,152

[22] Filed: Aug. 21, 1981

[30] Foreign Application Priority Data

Aug. 23, 1980 [GB] United Kingdom ................ 8027519
Nov. 26, 1980 [GB] United Kingdom ................ 8037841

[51] Int. Cl.$^3$ .................... C07C 101/24; C07C 87/26
[52] U.S. Cl. ................ 560/169; 260/112.5 R; 560/39; 560/41; 562/448; 562/449; 562/561; 562/565; 564/157; 564/159; 564/164; 564/182; 564/187; 564/197; 564/198; 564/215; 564/509; 424/177; 424/314; 424/319; 424/325
[58] Field of Search ............... 260/112.5 R; 560/39, 560/41, 169; 562/448, 449, 561, 565; 564/157, 159, 164, 182, 187, 197, 198, 215, 509

[56] References Cited

U.S. PATENT DOCUMENTS

| | | | |
|---|---|---|---|
| 2,662,915 | 12/1953 | Lontz | 562/574 |
| 4,323,704 | 4/1982 | Metcalf | 560/169 |
| 4,325,961 | 4/1982 | Kollonitsch | 560/169 |
| 4,326,071 | 4/1982 | Bey | 562/561 |

OTHER PUBLICATIONS

Mamont, Biochem. Biophys. Res. Comm., 81, p. 58, (1978).
Metcalf, J. Am. Chem. Soc., 100, p. 255, (1978).
Kollonitsch, Nature, 274, p. 906, (1978).

*Primary Examiner*—Michael L. Shippen
*Attorney, Agent, or Firm*—Gary D. Street; Raymond A. McDonald

[57] ABSTRACT

Fluorinated alkenylene diamine compounds are inhibitors of ornithine decarboxylase enzyme in vivo and have the following formula:

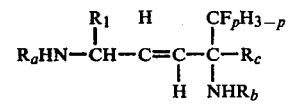

wherein:
$R_a$ represents hydrogen or $R_2$, where $R_2$ is as defined below;
$R_b$ represents hydrogen or, when $R_a$ is hydrogen, $R_2$, where $R_2$ is as defined below;
$R_c$ represents hydrogen or $-COR_3$, where $R_3$ is as defined below;
$R_1$ represents hydrogen or $C_1-C_6$ alkyl;
each $R_2$, independently, represents $C_2-C_5$ alkylcarbonyl, phenylcarbonyl, phenyl-($C_1-C_4$ alkyl) carbonyl, or an aminocarboxylic acid residue derived by removal of an hydroxy group from a carboxy moiety of an L-aminocarboxylic acid;
$R_3$ represents hydroxy, or, when $R_a$ and $R_b$ are both hydrogen, $C_1-C_8$ alkoxy, $-NR_4R_5$, where $R_4$ and $R_5$ are as defined below, or an aminocarboxylic acid residue derived by removal of an hydrogen atom from the amino moiety of an L-aminocarboxylic acid;
$R_4$ and $R_5$, independently, represent hydrogen or $C_1-C_4$ alkyl; and
p represents 1 or 2.

14 Claims, No Drawings

FLUORINATED PENTENE DIAMINE DERIVATIVES

FIELD OF THE INVENTION

This invention relates to novel fluorinated alkenylene diamine compounds having the following general formula:

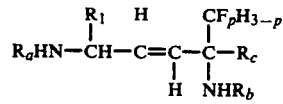

wherein:

$R_a$ represents hydrogen or $R_2$, where $R_2$ is as defined below;

$R_b$ represents hydrogen or, when $R_a$ is hydrogen, $R_2$, where $R_2$ is as defined below;

$R_c$ represents hydrogen or —$COR_3$, where $R_3$ is as defined below;

$R_1$ represents hydrogen or $C_1$-$C_6$ alkyl;

each $R_2$, independently, represents $C_2$-$C_5$ alkylcarbonyl, phenylcarbonyl, phenyl-($C_1$-$C_4$ alkyl) carbonyl, or an aminocarboxylic acid residue derived by removal of an hydroxy group from a carboxy moiety of an L-aminocarboxylic acid;

$R_3$ represents hydroxy, or, when $R_a$ and $R_b$ are both hydrogen, $C_1$-$C_8$ alkoxy, —$NR_4R_5$, where $R_4$ and $R_5$ are as defined below, or an aminocarboxylic acid residue derived by removal of an hydrogen atom from the amino moiety of an L-aminocarboxylic acid;

$R_4$ and $R_5$, independently, represent hydrogen or $C_1$-$C_4$ alkyl; and p represents 1 or 2.

The compounds in vivo are inhibitors of ornithine decarboxylase, an enzyme which is involved in polyamine formation in organisms. The invention also provides pharmaceutical compositions comprising said compounds, methods of medical treatment using said compounds, and processes for preparing said compounds.

BACKGROUND OF THE INVENTION

The decarboxylation of ornithine to putrescine, a reaction catalyzed by the enzyme ornithine decarboxylase (ODC), is the first step in the biosynthesis of the polyamines known as spermidine and spermine. Spermidine is formed by the transfer of an activated aminopropyl moiety from S-adenosyl S-methyl homocysteamine to putrescine, while spermine is formed by the transfer of a second aminopropyl group to spermidine. S-Adenosyl S-methyl homocysteamine is formed by the decarboxylation of S-adenosylmethionine (SAM), a reaction catalyzed by the enzyme S-adenosylmethionine decarboxylase (SAM-DC).

The polyamines, which are found in animal tissues and microorganisms, are known to play an important role in cell growth and proliferation. The onset of cell growth and proliferation is associated with both a marked increase in ODC activity and an increase in the levels of putrescine and the polyamines. Although the exact mechanism of the role of the polyamines in cell growth and proliferation is not known, it appears that the polyamines may facilitate macromolecular processes such as DNA, RNA, or protein synthesis. Polyamine levels are known to be high in embryonic tissue; in the testes, ventral prostrate, and thymus; in tumor tissue; in psoriatic skin lesions; and in other cells undergoing rapid growth or proliferation.

Since putrescine is the precursor of both spermidine and spermine, it is apparent that blockade of the conversion of ornithine to putrescine, such as by inhibition of ODC, should lower intercellular polyamine levels and should provide a wide range of useful physiological effects. Inhibitors of ODC should, thus, provide a means for treating infections caused by the proliferation of certain microorganisms in which the polyamines are essential for replication; for treating certain animal diseases and disorders associated with rapid cell proliferation, such as malignant or non-malignant tumors, psoriasis, and prostatic hypertrophy; and for interrupting early embryogenesis in female mammals (contragestational activity).

It is apparent from the above that non-toxic inhibitors of ornithine decarboxylase would be useful pharmacological agents having a potentionally wide range of uses.

We have disclosed in U.K. Patent Specification No. 2001960A that inter alia compounds of the following Formula A are inhibitors of ornithine decarboxylase:

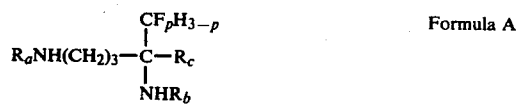

Formula A wherein:

$R_a$ represents hydrogen or $R_2$ where $R_2$ is as defined below;

$R_b$ represents hydrogen or $R_2$ where $R_2$ is as defined below;

$R_2$ represents $C_2$-$C_5$ alkylcarbonyl, $C_2$-$C_5$ alkoxycarbonyl, or —$COCH(R_6)NH_2$, where $R_6$ represents hydrogen, $C_1$-$C_4$ alkyl, benzyl or p-hydroxybenzyl;

$R_c$ represents —$COR_3$, where $R_3$ represents hydroxy, $C_1$-$C_8$ alkoxy, —$NR_4R_5$ where $R_4$ and $R_5$ independently represent hydrogen or $C_1$-$C_4$ alkyl, or —$NHCH(R_6)CO_2H$, where $R_6$ is as defined above; and p represents 1 or 2.

Further, we have disclosed in U.K. Patent Specification No. 2003876A that the analogues of said compounds of Formula A in which $R_c$ represents hydrogen are likewise ornithine decarboxylase inhibitors.

SUMMARY OF THE INVENTION

The compounds of the invention are represented by the following general Formula I:

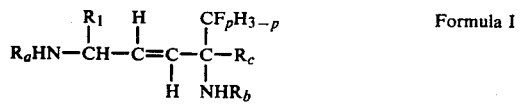

Formula I wherein:

$R_a$ represents hydrogen, or $R_2$, where $R_2$ is as defined below;

$R_b$ represents hydrogen or, when $R_a$ is hydrogen, $R_2$, where $R_2$ is as defined below;

$R_c$ represents hydrogen or —$COR_3$, where $R_3$ is as defined below;

$R_1$ represents hydrogen or $C_1$-$C_6$ alkyl;

each $R_2$ independently represents $C_2$-$C_5$ alkylcarbonyl, phenylcarbonyl, phenyl-($C_1$-$C_4$ alkyl) carbonyl, or an aminocarboxylic acid residue derived by removal of an hydroxy group from a carboxy moiety of an L-aminocrboxylic acid;

$R_3$ represents hydroxy, or, when $R_a$ and $R_b$ are both hydrogen, $C_1$-$C_8$ alkoxy, $-NR_4R_5$, where $R_4$ and $R_5$ are as defined below, or an aminocarboxylic acid residue derived by removal of a hydrogen atom from the amino moiety of an L-aminocarboxylic acid:

$R_4$ and $R_5$ independently represent hydrogen or $C_1$-$C_4$ alkyl; and p represents 1 or 2.

Pharmaceutically acceptable salts and individual optical isomers of the compounds of general Formula I are also within the scope of the invention.

The compounds of Formula I inhibit ornithine decarboxylase enzyme (ODC) in vivo, as evidenced by standard pharmacological test procedures performed in laboratory animals. As a consequence of ODC inhibition, the compounds can be used in general to decrease putrescine, spermidine, and/or spermine concentrations in cells undergoing rapid growth or proliferation. The administration of a compound of Formula I, therefore, provides a method for controlling undesirable cell growth or proliferation in mammals. The compounds of Formula I are useful pharmacological agents for treating those diseases or conditions that are known in the art to be characterized by rapid growth or proliferation associated with high ODC activity. In particular, the compounds are useful systemically for controlling the growth of tumor tissues in mammals and for controlling the growth of pathogenic parasitic protozoa in infected domestic animals and humans.

The compounds of Formula I can also be employed to study the presence and physiological function of ODC inhibition in biological systems and its relationship to pathological processes.

The compounds of Formula I wherein $R_a$ or $R_b$ is a group other than hydrogen or $R_c$ is a group other than hydrogen or carboxy do not inhibit ODC in vitro. In order to produce inhibition of ODC in vivo, said compounds must undergo biotransformation to the compounds of Formula I wherein $R_a$ and $R_b$ are both hydrogen and $R_c$ is hydrogen or carboxy, which compounds are inhibitors of ODC both in vitro and in vivo. The ODC activity of the compounds can be determined in vitro by the method described by B. Metcalf et al. *J. Am. Chem. Soc.*, 100, 2551 (1978). The ODC activity of the compounds of Formula I can be determined in vivo by the method of C. Danzin, *Biochemical Pharmacology*, 28, 627 (1979).

DETAILED DESCRIPTION OF THE INVENTION

In the above general Formula I, $R_a$ and $R_b$ both can be hydrogen or one of them can be hydrogen and the other can be $C_2$-$C_5$ alkylcarbonyl, phenylcarbonyl, phenyl-($C_1$-$C_4$ alkyl)carbonyl, or an aminocarboxylic acid residue derived by removal of an hydroxy group from the carboxy moiety of an L-aminocarboxylic acid. Preferably, $R_a$ and $R_b$ both represent hydrogen.

In the above general Formula I, $R_c$ represents hydrogen or the group $-COR_3$ in which $R_3$ represents hydroxy, or, when $R_a$ and $R_b$ are both hydrogen, $C_1$-$C_8$ alkoxy, $-NR_4R_5$ or an aminocarboxylic acid residue derived by removal of a hydrogen atom from the amino moiety of an L-aminocarboxylic acid. Said $R_4$ and $R_5$ independently represent hydrogen or $C_1$-$C_4$ alkyl. Preferably $R_c$ represents hydrogen, carboxy (i.e. $R_3$ is hydroxy) or alkoxycarbonyl (i.e. $R_3$ is $C_1$-$C_8$ alkoxy).

In the above general Formula I, $R_1$ represents hydrogen or $C_1$-$C_6$ alkyl, especially methyl.

When $R_3$ is an aminocarboxylic acid residue, it can be, for example, of the formula $-NHCH(R_6)CO_2H$, wherein $R_6$ is hydrogen, $C_1$-$C_4$ alkyl aminopropyl, aminobutyl, benzyl or p-hydroxybenzyl. Similarly, when $R_2$ is an aminocarboxylic acid residue, it can be, for example, of the formula $-COCH(R_6)NH_2$ or $-CO(CH_2)_nCH(NH_2)-CO_2H$, wherein $R_6$ is as defined above and n is 1 or 2. Examples of $R_2$ and $R_3$ residues are those derived from glycine, alanine, leucine, lysine, isoleucine, phenylalanine, tyrosine, glutamic acid and aspartic acid.

References in this Specification, including the claims, to an alkyl group or moiety mean a straight or branched chain alkyl group or moiety and, in the case of an alkyl group or moiety having structural isomers, includes all of those isomers and mixtures thereof unless a particular isomer is specified or clearly implied by the context.

Illustrative examples of straight or branched chain alkyl groups or moieties having 1 to 4 carbon atoms are methyl, ethyl, n-propyl, iso-propyl and n-butyl.

Illustrative examples of straight or branched chain alkyl groups or moieties having 1 to 6 carbon atoms are those specified above having 1 to 4 carbon atoms and n-pentyl, neo-pentyl, n-hexyl and iso-hexyl.

Illustrative examples of straight or branched chain alkyl groups or moieties having 1 to 8 carbon atoms are those specified above having 1 to 6 carbon atoms and n-heptyl, 5-methylhexyl and n-octyl.

It will be appreciated that the compounds of the invention specified in Table I below are the fluorinated methyl dehydro analogues of the respective specified naturally occurring amino acid or diamine.

TABLE I

| Formula I | | | | |
|---|---|---|---|---|
| $R_1$ | $R_a$ | $R_b$ | $R_c$ | Analogue |
| H | H | H | $CO_2H$ | ornithine |
| H | H | H | H | putrescine |

In the above general Formula I, p represents 1 or 2. It will be appreciated that when p represents 1, the compounds of the invention are mono-fluoromethyl derivatives and that when p represents 2 they are di-fluoromethyl derivatives.

As indicated in general Formula I, the compounds of the invention are in the trans, or entgegen, configuration. Trans isomers are indicated in the nomenclature used in this Specification, including the claims, by the letter "E". The invention includes, of course, non-toxic mixtures of said isomer with its cis isomer.

Illustrative examples of pharmaceutically acceptable salts of the compounds of this invention include non-toxic acid addition salts formed with inorganic acids, such as hydrochloric, hydrobromic, sulfuric and phosphoric acid, or with organic acids, such as, organic carboxylic acids, for example salicylic, maleic, malonic, tartaric, citric and ascorbic acids, and organic sulfonic acids, for example methane sulfonic acid; and non-toxic salts formed with inorganic or organic bases, such as, hydroxides of alkali metals, for example, sodium, potassium and lithium, alkaline earth metals, for example, calcium and magnesium, light metals of Group III A, for example, aluminium, organic amines, such as, primary, secondary or tertiary amines, for example, cyclohexylamine, ethylamine, methylaminoethanol, ethanol-amine and piperidine. The salts are prepared by conventional means.

In one embodiment of the invention, there are provided compounds of the following general Formula IA:

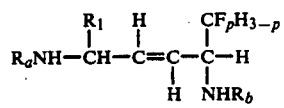

Formula IA wherein:
$R_1$, $R_a$, $R_b$ and p are defined in connection with Formula I;
and pharmaceutically acceptable salts thereof.

In another embodiment of the invention, there are provided compounds of the following general Formula IB:

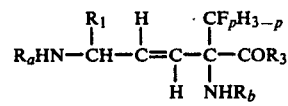

Formula IB wherein:
$R_1$, $R_3$, $R_a$, $R_b$ and p are as defined in connection with Formula I;
and pharmaceutically acceptable salts thereof.

Illustrative examples of compounds of the present invention are the following:
1-fluoro-2,5-diamino-3-(E)-pentene;
1,1-difluoro-2,5-diamino-3-(E)-pentene;
1-fluoro-2,5-diamino-3-(E)-hexene;
2-fluoromethyl-2,5-diamino-3-(E)-penten-1-oic acid;
2-difluoromethyl-2,5-diamino-3-(E)-penten-1-oic acid;
ethyl 2-fluoromethyl-2,5-diamino-3-(E)-penten-1-oate;
ethyl 2-difluoromethyl-2,5-diamino-3-(E)-penten-1-oate;
2-fluoromethyl-2,5-diamino-3-(E)-penten-1-amide;
2-difluoromethyl-2,5-diamino-3-(E)-penten-1-amide;
N-(β-phenethyl) 2-fluoromethyl-2,5-diamino-3-(E)-penten-1-amide;
N-(1-difluoromethyl-4-amino-2-(E)-butenyl)-2-aminoacetamide;
N-(4-fluoromethyl-4-amino-2-(E)-butenyl)butyramide;
2-fluoromethyl-2-benzamino-5-amino-3-(E)-penten-1-oic acid;
1-fluoro-2-amino-5-(3'-phenylpropionylamino)-3-(E)-pentene;
1,1-difluoro-2,5-diamino-3-(E)-hexene;
1-fluoro-2,5-diamino-3-(E)-heptene;
1,1-difluoro-2,5-diamino-3-(E)-heptene.

As used herein, the term "tumor tissue" means both benign and malignant tumors or neoplasms, and includes leukemias, lymphomas, melanomas, and sarcomas. The term "controlling the growth of tumor tissue" as used herein means slowing, interrupting, arresting, or stopping the growth of a rapidly proliferating tumor in a warm blooded animal. It should be understood that the administration of a compound of the Formula I does not provide a "cure" for the tumor in the sense that the tumor tissue is destroyed or totally eliminated from the animal being treated.

For controlling the growth of tumor tissues, a compound of Formula I can be administered to the patient in conjunction with other therapeutic methods or in combination with cytotoxic drugs known in the art to be useful for cancer chemotherapy. For example, a compound of Formula I can be administered in conjunction with surgical excision of the tumor or with radiation therapy, hormonal treatment, immunotherapy, or local heat therapy. Moreover, in a preferred manner, a compound of Formula I can be administered to a patient in combination with a chemical cytotoxic agent known in the art to be useful for tumor chemotherapy. When such combination therapy is employed for the treatment of a tumor, the cancer chemotherapeutic agent may be administered at a dosage known in the art to be effective for treating the tumor. However, a compound of Formula I may produce an additive or synergistic effect with a chemotherapeutic agent against a particular tumor. Thus, when such combination antitumor therapy is used, the dosage of the chemotherapeutic agent administered may be less than that administered when the agent is used alone. In combination with a compound of Formula I, the chemotherapeutic agent may, therefore, be administered at a lower dosage level or at less frequent intervals as compared to the chemotherapeutic agent when used alone.

In combination with a compound of Formula I, any cancer chemotherapeutic agent may be employed. Drugs commonly used for cancer chemotherapy are described in *The Medical Letter*, Vol. 22, No. 24 (Issue 571), Nov. 28, 1980, Published by the Medical Letter, Inc., New Rochelle, N.Y., 10801. Illustrative examples of cytotoxic chemotherapeutic agents are cyclophosphamide, methotrexate, prednisone, 6-mercaptopurine, procarbozine, daunorubicin, vincristine, vindesine, vinblastine, chlorambucil, cytosine arabinoside, 6-thioguanine, thio TEPA, 5-fluorouracil, 5-fluoro-2-deoxyuridine, 5-azacytidine, nitrogen mustard, 1,3-bis(2-chloroethyl)-1-nitrosourea (BCNU), 1-(2-chloroethyl)-3-cyclohexyl-1-nitrosourea (CCNU), busulfan, adriamycin, bleomycin, cycloleucine or methylglyoxal bis(guanylhydrazone) (MGBG). Other cancer chemotherapeutic agents will be apparent to those skilled in the art.

The effect of the compounds of Formula I for the control of the growth rate of rapidly proliferating tumor tissue can be assessed in standard animal tumor models after oral or parenteral administration. For example, the antitumor effects can be demonstrated in the following models: (a) L1210 leukemia in mice, (b) EMT 6 tumor in Balb/C mice, (c) 7,12-dimethylbenzanthracene-induced (DMBA-induced) mammary tumor in rats, or (d) Morris 7288 C or 5123 hepatoma in Buffalo rats. In addition, the antitumor effects of the compounds in combination with chemotherapeutic agents can be demonstrated in animal models.

In general in animal tumor models, the compounds of Formula I effectively reduce tumor growth rate systematically at a daily dose of from about 20 mg/kg to about 400 mg/kg (body weight). As will be apparent to those skilled in the art, the effective dosage will vary depending on the compound employed, the nature and severity of the particular neoplasm being treated, the route of administration, and the species being treated. Treatment should be initiated at lower doses, the dosage thereafter being increased until the desired effect on tumor growth is achieved.

When, in the treatment of a malignant neoplastic disease, a compound of Formula I is administered in combination with a chemotherapeutic agent, the therapeutic effect of the chemotherapeutic agent may be potentiated in that the remission produced by the chemotherapeutic agent may be enhanced and regrowth of the tumor tissue may be slowed or prevented. Use of such combination therapy therefor allows smaller doses or fewer individual doses of the chemotherapeutic agent to be employed. Thus, the detrimental and/or debilitating side effects of the chemotherapeutic agent are minimized while, at the same time, the antitumor effects are enhanced. The term "combination therapy" contemplates the administration of a compound of Formula I immediately prior to the beginning of chemotherapy, concommitantly with chemotherapy, or during the period of time immediately following cessation or discontinuance of chemotherapy. Preferably, the patient is treated with a compound of Formula I for about 1 to 14 days, preferably 4 to 14 days, prior to the beginning of chemotherapy, and, thereafter, on a daily basis during the course of such therapy. Daily treatment with the compound of Formula I can be continued for a period after the last dose of the chemotherapeutic agent is administered.

When chemotherapy results in remission of the tumor and all tumor cells are not destroyed, regrowth of the tumor may be prevented or slowed indefinitely by continued treatment with a compound of Formula I. Thus, a compound of Formula I can be administered to stop or slow the growth of the tumor during the periods when chemotherapy using a cytotoxic agent may be temporarily discontinued.

A preferred cytotoxic agent for combination therapy with a compound of Formula I is methylglyoxal bis(-guanylhydrazone), herein referred to as MGBG, which is also an inhibitor of S-adenosyl methionine decarboxylase. The activity of MGBG as a chemotherapeutic agent in the treatment of neoplastic diseases is well documented. For example, W. A. Knight et al. *Cancer Treat. Rep.*, 43, 1933, (1979) have reported that a dose of MGBG administered intravenously once or twice week to patients in the advanced stages of carcinoma of the bladder, esophagus, lung, pancreas, colon, kidney, breast and prostate, oat cell carcinoma, adenocarcinoma, lymphoma, hepatoma, melanoma, leukemia, or Edwing's sarcoma produced measurable regression of the tumor in many of the patients treated and complete disappearance of the disease in two of the 65 treated patients.

The amount of MGBG to be administered may be the same as the amount known in the art to be effective for tumor therapy. Effective and non-toxic dosages are determined by the physician in each case, taking into account the condition of the individual patient. For example, a dosage of 250–500 mg per meter$^2$ of body surface area may be infused once or twice weekly in 100 ml of aqueous 5% dextrose solution over a 30 min period. Combination therapy with a compound of Formula I improves the response of the tumor tissue to the cytotoxic effect of MGBG and permits the use of a smaller individual dose of MGBG and a shorter course of treatment than would be required with the use of MGBG alone.

Suitable dosages of the compounds of Formula I for use in combination therapy with MGBG or other cancer chemotherapeutic agents can be any amount effective in inhibiting polyamine biosynthesis sufficiently to control the tumor growth rate or to achieve a heightened response to the cytotoxic agent administered in conjunction therewith.

The term "controlling the growth of pathogenic parasitic protozoa", as used herein, means slowing, interruting, arresting, or stopping the replication of the protozoa in an infected host. The compounds of Formula I are particularly useful against *T.b. brucei* (which causes trypanosomiasis in cattle), *T.b. rhodesiense*, (which causes human sleeping sicksickness), the coccidia, for example, *Eimeria tenella* (which causes intestinal coccidiosis in fowl (e.g. chickens, turkeys, and ducks)) and the exoerythrocytic form of plasmodia, for example, *plasmodium falciparum* (which causes human malaria).

The antiprotazoal activity of the compounds of Formula I can be demonstrated in vivo or in vitro in standard microbiological test procedures. For example, the activity of the compounds against *T.b. brucei*, and *T.b. rhodesiense* can be determined in infected mice by administering the test compound ad lib daily (3 to 15 days post infection) as a solution in the drinking water at a concentration of 0.5 to 2%. Activity is indicated by an increase in survival time (as compared to untreated controls) or by the absence of parasites in the blood. The activity of the compounds against the coccidia can be determined in infected chickens, for example those infected with *E. tenella* by administering the test compound daily ad lib (from one day pre injection to five days post infection) as a solution in the drinking water at a concentration of 0.5 to 2%. The cecal lesions are evaluated by a standard lesion scoring procedure. (See Reid. *Am. J. Vet Res.*, 30, 447 (1969) and *Avian Coccidiosis*, P. Long. Editor, British Poultry Science, Ltd., Edinburgh). The activity of the compounds against malaria (*p.faleiparum*) can be determined by a standard in vitro plate culture test (See K. Rieckmann et al., *Lancet*, 1, 22 (1978)). Antimalarial activity can also be determined in special strains of mice infected with the exoerythrocitic form of *p.berghei*. In this test, the compound is administered ad lib in drinking water at a concentration of from 0.2 to 1.0% starting two days preinfection and continuing 28 days post-infection. Activity is measured by a significant decrease in deaths as compared to controls or by a significant increase in survival time.

The compounds of Formula I wherein $R_c$ is —COR$_3$ are also capable of interrupting embryogenesis in female mammals when administered systematically. Thus, the compounds are useful as contragestational agents in female mammals when it is desired to terminate early pregnancy. The contragestational activity of the compounds can be demonstrated in mice by the method of J. Fozard, *European Journal of Pharmacology*, 65, 379 (1980). When tested by the aforesaid method, 2-fluoromethyl-2,5-diamino-3-(E)-penten-1-oic acid inhibited gestation at a dose of 80 mg/kg (body weight) administered by the S.C. route every six hours on the 8th day of gestation, as evidenced by a significant decrease in the number of viable feti per gravid female as compared to controls. In general, an effective daily dose of the compounds of Formula I, wherein $R_c$ is —COR$_3$, for terminating pregnancy in warm-blooded mammals is from 10 mg/kg to 1 g/kg, preferably 10 to 100 mg/kg, administered after fertilisation during the period between Standard Stages 8–16 of gestation as defined by E. Wischi (See Tables 26–27, pages 82–92, *Biology Data Book*, Altman and Dittmer, Editors, Published by the Federation of American Societies for Experimental Biology, Washington, D.C., 1964). The period of treatment will vary with the species. In humans, the period of treatment will extend from the 6th–7th day of gestation of the 27th day.

Compounds of Formula I may have one or more additional uses, for example to treat epidermal hyperplasia (e.g. psoriasis) or prostatic hypertrophy.

The compounds of this invention can be administered in various manners to achieve the desired effect. The compounds can be administered alone or in the form of pharmaceutical preparations either orally or parenterally, for example, subcutaneously, intravenously or interperitoneally. The amount of novel compound administered will vary and can be any effective amount. Depending upon the patient, the condition being treated and the mode of administration, the effective dosage of the compound administered may vary from about 5 mg/kg to about 100 mg/kg, of body weight of the patient per day. Unit doses of these compounds can contain, for example, from about 10 mg to 300 mg of the compounds and may be administered, for example, from 1 to 4 times daily.

The term "unit dosage form" is used herein to mean a single or multiple dose form containing a quantity of the active ingredient in admixture with or otherwise in association with the diluent or carrier, said quantity being such that one or more predetermined units are normally required for a single therapeutic administration. In the case of multiple dose forms such as liquids or scored tablets, said predetermined unit will be one fraction, such as a 5 ml (teaspoon) quantity of a liquid or a half or quarter of a scored tablet, of the multiple dose form.

In the composition aspect of the invention there are provided pharmaceutical formulations in which form the active compounds of the invention will normally be utilized. Such formulations are prepared in a manner well known per se in the pharmaceutical art and usually comprise at least one active compound of the invention in admixture or otherwise in association with a pharmaceutically acceptable carrier or diluent therefor. For making these formulations the active ingredient will usually be mixed with a carrier, or diluted by a diluent, or enclosed or encapsulated in a capsule, sachet, cachet, paper or other container. A carrier or diluent may be solid, semi-solid or liquid material which serves as a vehicle, excipient or medium for the active ingredient. Suitable carriers or diluents are well known per se.

The formulations of the invention may be adapted for enteral or parenteral use and may be administered to the patient in the form of tablets, capsules, suppositories, solutions, suspensions or the like.

In the specific examples included hereinbelow illustrative examples of suitable pharmaceutical formulations are described.

Methods of preparing the compounds of Formula I will now be described. If in any of the reaction steps described an amino group of a reactant would be involved in an unwanted reaction under the relevant reaction conditions, the amino group will be protected in manner known per se by introduction of an appropriate protecting group. The protecting group will be chosen having regard to the nature of the relevant reaction and ease of removal to free the amino group. The protecting group can be selected from, for example, acyl, for example, lower alkanoyl, e.g. acetyl, propionyl, trifluoroacetyl, and the like; aroyl, e.g. benzoyl, toluoyl and the like; lower alkoxycarbonyl, for example methoxycarbonyl, ethoxycarbonyl, tert-butoxycarbonyl and the like; carbobenzoxy, benzenesulfonyl and tosyl. Both amino hydrogen atoms can be substituted by a single protecting group such as, for example phthalyl.

The protecting groups are introduced in manner known per se by, for example, reaction of the amine with a lower alkanoyl or aroyl chloride, anhydride, sulfonylchloride, tert-butoxycarbonyloxyimino-2-phenylacetonitrile (BOC-ON), or di-tert-butyl dicarbonate ((BOC)$_2$O).

Removal of the protecting group after the required reaction has been completed can be carried out in manner known per se for the relevant protecting group. Usually, said removal will be by hydrolytic cleavage using a strong organic or mineral acid such as, for example, trifluoroacetic acid, hydrochloric acid and the like acids; or by hydrogen chloride gas under anhydrous conditions. The use of conditions which will reduce the olefinic double bond or of reactants, such as hydrobromic acid, which will react with the olefinic double bond must be avoided. Solvents used will be chosen dependent upon the conditions of protecting group removal. For example, ethers such as, for example, diethylether can be used for cleavage using hydrogen chloride gas.

The compounds of Formula I in which $R_a$ and $R_b$ both represent hydrogen and $R_c$ represents hydrogen, carboxy or alkoxycarbonyl can be prepared in manner known per se from the corresponding compound of the following general Formula II:

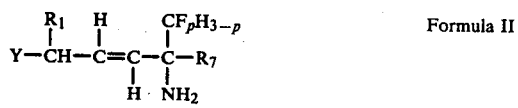

Formula II wherein:

$R_1$ and p are defined in connection with Formula I;

$R_7$ represents hydrogen, cyano or $C_2$–$C_9$ alkoxycarbonyl; and

Y represents a leaving group such as bromine, chlorine, iodine, tosyloxy (i.e. toluene-p-sulfonyloxy) or mesyloxy (i.e. methanesulfonyloxy).

The reaction can proceed via the corresponding phthalimido, isocyanato or urotropino derivative as described below.

The amino group in the compound of Formula II will be protected in manner known per se during the reaction by a suitable subsequently removable protecting group or groups. The protecting group preferably is phthaloyl. When proceeding via the phthalimido or isocyanate derivative when p is 1, it is necessary to use a protecting group which does not leave any hydrogen atom on the amino group in order to obtain the desired compound of Formula I. Usually, the protecting group will be selected so that it is removed during the final step in the conversion of the compound of Formula II into the corresponding compound of Formula I.

The compounds of Formula II or the aminoprotected derivatives thereof can be treated with an alkali metal phthalimide, especially sodium or potassium phthalimide, in a polar organic solvent, such as for example, dimethylformamide, dimethylsulfoxide or hexamethylphosphoric triamide, to form the corresponding phthalimido derivative. Conveniently one to three equivalents of the phthalimide salt are used per equivalent of compound of Formula II at a temperature of 25° to 200° C. for a period of 0.5 to 3 hours.

When $R_7$ is hydrogen or alkoxycarbonyl, the phthalimido derivative can be converted into the required compound of Formula I by heating with a reactant such as hydrazine or methylamine in a polar organic solvent such as, for example, an alkanol, preferably ethanol. Preferably hydrazine hydrate is used in an amount of about 2 equivalents per equivalent of phthalimido derivative. Suitably, the conversion is performed at 50° to 100° C., preferably under reflux conditions, for a period of 3 to 24 hours.

The phthalimido derivative of Formula II also can be converted into the required compound of Formula I by heating with a strong mineral acid such as hydrochloric acid or sulfuric acid. Said heating also hydrolyses any cyano group represented by $R_7$ to a carboxy group. Preferably a mixture of hydrochloric and acetic acid is used at a temperature of about 95° C. for about 24 hours. Acids, such as hydrobromic acid, which are reactive towards olefinic double bonds cannot be used.

In an alternative process, the compound of Formula II is treated with an alkali metal isocyanate, especially sodium or potassium isocyanate, and the resultant isocyanato derivative subsequently hydrolysed to the required compound of Formula I. The reaction conditions can be the same as those discussed above with reference to conversion of a compound of Formula II to a compound of Formula I via the phthalimido derivative in which the phthaloyl group is removed by acid hydrolysis.

In another alternative process, the compound of Formula II is treated with hexamethylenetetramine in an organic solvent, such as a $C_1-C_4$ alkanol or chloroform, to form the corresponding urotropine (i.e. hexamethylenetetrammonium) salt. Conveniently, the reaction can be carried out at about ambient temperature for a period of 0.5 to 24 hours. The urotropine salt can be converted into the required compound of Formula I by heating with an aqueous acid, such as hydrochloric acid, preferably under reflux conditions and preferably under an inert atmosphere, for example nitrogen or argon. As mentioned above, acids, such as hydrobromic acid, which are reactive to olefinic double bonds cannot be used. Moreover, when the leaving group Y is bromine or iodine, bromide or iodide respectively is displaced before the hydrolysis by, for example, addition of hydrochloric acid and subsequent removal of the aqueous phase under reduced pressure at room temperature.

Compounds of Formula II can be obtained in manner known per se from the corresponding compounds of the following general Formula III:

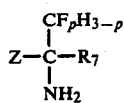

Formula III wherein:

Z represents $CH_2=CH-CH_2-$ or $CH_2(R_1)-CH=CH-$; and $R_1$, $R_7$, and p are as defined in connection with Formula II.

Compounds of Formula II in which Y represents halogen can be obtained by allylic halogenation of the corresponding compound of Formula III. Conveniently, the allylic halogenation can be carried out by the Wohl-Ziegler Reaction in which the compound of Formula III is treated with an N-haloamide, preferably an N-halosuccinimide, in the presence of a free-radical initiator as a peroxide or labile azo compound and under light irradiation.

The allylic halogenation referred to above is particularly suitable for the preparation of compounds of Formula II because the product is predominantly in the trans configuration regardless of the configuration of the reactant of Formula III.

Compounds of Formula II in which Y represents tosyloxy or mesyloxy can be obtained by allylic oxidation of the corresponding compound of Formula III to form the corresponding alcohol and subsequently treating the alcohol with tosyl chloride or mesyl chloride in the presence of a base such as pyridine.

Compounds of Formula III in which $R_7$ represents cyano can be obtained from the corresponding compounds of the following general Formula IV by treatment with an alkali metal or ammonium cyanide, such as, for example, sodium cyanide in water in the presence of a water soluble ammonium salt of a strong acid, especially ammonium chloride.

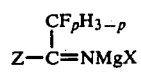

Formula IV wherein:

Z and p are as defined in connection with Formula III and

X represents bromine, iodine or, when Z is allylic, chlorine.

Compounds of Formula III in which $R_7$ represents hydrogen, can be obtained from the corresponding compound of Formula IV by reduction with a reducing agent, such as a borohydride, which selectively reduces the imino group.

Compounds of Formula III in which $R_7$ represents alkoxycarbonyl can be obtained by hydrolysis of the corresponding compound of Formula III in which $R_7$ represents cyano in the presence of an acid, such as hydrochloric acid, and the corresponding alcohol.

Compounds of Formula IV can be obtained by treatment of the corresponding Grignard reactant of the following general Formula V with the corresponding fluorinated acetonitrile of the following general Formula IV:

Formula V wherein Z and X are as defined in connection with Formula IV;

Formula VI wherein p represents 1 or 2.

The Grignard reactants of Formula V can be prepared in manner known per se from, for example, the corresponding halides of the following general Formula VII and magnesium turnings in an appropriate solvent for Grignard type reactions.

Formula VII wherein Z is as defined in connection with Formula V.

The halides of Formula VII are known or can be prepared by analogous processes for obtaining said known compounds.

Compounds of Formula II above in which $R_7$ represents hydrogen or cyano and Y represents bromine or iodine can also be obtained by boron tribromide or trialkylsilyliodide cleavage in manner known per se of an allylic compound of the following general Formula VIII:

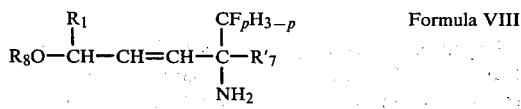

wherein:

$R_1$ and p are as defined in connection with Formula II, $R_7'$ represents hydrogen or cyano, and $R_8$ represents $C_1-C_4$ alkyl, preferably methyl.

Compounds of Formula VIII can be obtained from a corresponding compound of the following general Formula IX by the process steps described above for conversion of a compound of Formula VII into a compound of Formula III:

wherein $R_1$ and $R_8$ are as defined in connection with Formula VIII.

Compounds of Formula IX can be obtained in manner known per se from the corresponding compound of the following general Formula X by treatment with a $C_1-C_4$ alkoxide:

wherein $R_1$ is as defined in connection with Formula IX.

Compounds of Formula X can be obtained by a Wohl-Zeigler Reaction on the corresponding compound of the following general Formula XI using N-bromosuccinimide in the presence of a free radical initiator and under light irradiation.

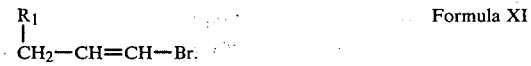

Compounds of Formula III also can be prepared in manner known per se from the corresponding compounds of the following general Formula XII:

wherein Z, $R_7$ and p are as defined in connection with Formula III except that $R_7$ cannot represent cyano when Z represents $R_1CH_2CH=CH-$.

The conversion of a compound of Formula XII into a compound of Formula III can be carried out by the Curtius Reaction (see, for example, Organic Reactions, Vol. III at page 338) which proceeds via the corresponding acyl azide and isocyanate.

In an alternative conversion of a compound of Formula XII into a compound of Formula III, the Schmidt Reaction (see, for example, Organic Reactions, Vol. III at page 308) can be used in which the compound of Formula XII is treated with hydrazoic acid in the presence of a strong mineral acid such as, for example sulfuric acid.

A compound of Formula XII also can be converted into a compound of Formula III by the Hofmann Rearrangement (see, for example, Organic Reactions Vol. III at page 268) in which the primary amide of the compound of Formula XII is converted to an amine via the corresponding N-haloamide and isocyanate. According to a preferred procedure for use in the present invention, the amide is treated with iodobenzene bis (trifluoroacetate) in acetonitrile-water (see, for example, Radhakrishna et al. J. Org. Chem. 44, (1979), 1746/7). The amide can be obtained from the acid of Formula XII in conventional manner by forming the acid chloride and treating said chloride with an ammonium salt.

The compounds of Formula XII can be obtained by hydrolysis in manner known per se of the corresponding compounds of the following general Formula XIII:

wherein:

Z and p are as defined in connection with Formula XII;

$R_7''$ represents cyano or $-CO_2R_{10}$ where $R_{10}$ is as defined below;

$R_9$ represents a $C_1-C_4$ alkyl group or benzyl; and $R_{10}$ represents $C_1-C_8$ alkyl or benzyl.

When a compound of Formula XII is required in which $R_7$ represents hydrogen, a corresponding diester of Formula XIII in which $R_9$ and $R_{10}$ independently represent $C_1-C_4$ alkyl, preferably tert. butyl, or benzyl is hydrolysed and decarboxylated by treatment with an acid.

When a compound of Formula XII is required in which $R_7$ is cyano or alkoxycarbonyl, the reaction conditions and groups $R_9$ and $R_{10}$ are chosen to selectively hydrolyse the $-CO_2R_9$ group. It is preferred however that in the compound of Formula XIII, $R_9$ is tert-butyl and, if present, $R_{10}$ is a straight chain alkyl group so that mild acid hydrolysis conditions using, for example trifluoroacetic acid, will hydrolyse the tert-butyl group $R_9$ but not the $R_7''$ group.

Compounds of Formula XIII can be obtained in manner known per se by mono- or di-fluoromethylation of the corresponding compound of the following general Formulae XIV or XV:

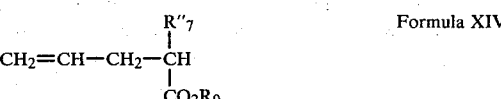

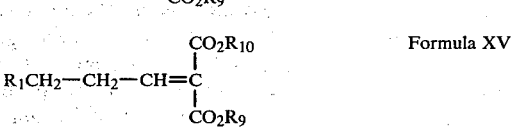

In Formula XIV, $R_7''$ and $R_9$ are as defined in connection with Formula XIII and in Formula XV, $R_1$ is as defined in connection with Formula I and $R_{10}$ is as defined in connection with Formula XIII.

When a compound of Formula XIV is fluoromethylated, the product is a compound of Formula XIII in which Z represents $CH_2=CH-CH_2-$ and, when a compound of Formula XV is fluoromethylated, the product is a compound of Formula XIII in which Z represents $CH_2(R_1)-CH=CH-$.

The fluoromethylation can be carried out by adding an excess of fluoromethylating agent of the following general Formula XVI to a solution in an aprotic solvent of a carbanion derived from the compound of Formula XIV or Formula XV:

$$CF_pH_{3-p}W \qquad \text{Formula XVI}$$

wherein:

p represents 1 or 2; and

W represents bromine, iodine or, preferably, chlorine.

The carbanion usually is obtained by treating the compound of Formula XIV or Formula XV in the aprotic solvent with a base.

The compounds of Formula XIV can be prepared in manner known per se by alkylation of a malonate or cyanoacetate of the following general Formula XVII with an allylhalide of the following general Formula XVIII:

$$R_7''-CH_2-CO_2R \qquad \text{Formula XVII}$$

$$CH_2=CH-CH_2-X' \qquad \text{Formula XVIII}$$

In Formula XVII, $R_7''$ and $R_9$ are as defined in connection with Formula XIV and, in Formula XVIII, X' represents bromine or chlorine. Suitably the alkylation is carried out in an organic solvent in the presence of a strong base which abstracts a proton from the malonate or cyanoacetate.

The compounds of Formula XV can be prepared in manner known per se by condensation of a malonate of following general Formula XVIIA with an aldehyde of the following general Formula XIX $$R_{10}O_2C-CH_2-CO_2R_9 \qquad \text{Formula XVIIA}$$

$$R_1CH_2-CH_2-CHO \qquad \text{Formula XIX}$$

In Formula XVIIA, $R_9$ and $R_{10}$ are as defined in connection with Formula XV and, in Formula XIX, $R_1$ is as defined in connection with Formula XV. Suitably, the condensation is carried out by refluxing a solution of the said reactants in acetic anhydride.

It will be appreciated that the color of some of the reaction steps in the process routes described above can be changed. For example, a terminal amino or protected terminal amino group can be introduced into the compound of Formula XIII using the same procedure as described for converting the compound of Formula III into a compound of Formula I and subsequently converting, if necessary after protecting the amino group, the resultant compound (which is a compound of the following general Formula XX or an amino-protected derivative thereof) into a compound of Formula I by the same procedure as described above for converting a compound of Formula XIII into a compound of Formula III.

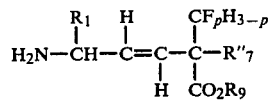

Formula XX wherein p, $R_7''$ and $R_9$ are as defined in connection with Formula XIII. Suitably, the phthalimido intermediate in the said formation of a terminal amino group is subjected to the necessary reaction conditions to convert the $-CO_2R_9$ and, if necessary, $-R_7''$ groups into the required group(s) and subsequently the phthaloyl group is removed.

The amides of Formula I derived from one of the amino groups can be prepared directly or indirectly in manner known per se from the corresponding diamines of Formula I. In some circumstances, it may be necessary to protect the non-reacting amino group prior to the reaction. Conveniently, the protected reactant can be obtained by selective hydrolysis of a derivative in which the amino group required for reaction is protected in the form of a urotropine salt and the other amino group is protected in the form a phthalimido group. Said derivatives readily can be prepared by appropriate choice of reaction sequence from those discussed above for the general preparation of compounds of Formula I.

The amides of Formula I wherein $R_a$ or $R_b$ is alkylcarbonyl can be obtained in manner known per se by treatment of the corresponding compounds of Formula I wherein $R_a$ or $R_b$ is hydrogen with the corresponding acid halide, especially acid chloride, or acid anhydride in water in the presence of a base.

The amides of Formula I wherein $R_a$ or $R_b$ is an aminocarboxylic acid residue can be prepared in manner known per se by treating the corresponding compound of Formula I wherein $R_a$ or $R_b$ is hydrogen with the corresponding aminocarboxylic acid in an anhydrous organic solvent in the presence of a dehydrating agent, followed by acid or base hydrolysis.

The esters of Formula I wherein $R_c$ is alkoxycarbonyl can be obtained in manner known per se from the corresponding acids of Formula I wherein $R_c$ is carboxy by esterification with the corresponding alcohol or by conversion into the corresponding acid chloride and alcoholysis of said acid chloride with the corresponding alcohol.

The compounds of Formula I wherein $R_c$ represents $-CONR_4R_5$ can be obtained in manner known per se from compounds of Formula I wherein $R_c$ represents carboxy and the amino groups are protected against reaction, by conversion into the corresponding acid chloride and subsequent amidation of said acid chloride with the corresponding amine (i.e. $HNR_4R_5$) or, when $R_4$ and $R_5$ are both hydrogen, with a compound which is a potential source of ammonia such as, for example, hexamethylenetetramine in the presence of a base such as triethylamine.

Compounds of Formula I wherein $R_c$ is an aminocarboxylic acid residue can be prepared by treating in manner known per se a compound of Formula I wherein $R_c$ represents carboxy or alkoxycarbonyl and the amino groups are protected against reaction, with a $C_1-C_4$ alkyl ester of the corresponding amino-acid, and, when $R_c$ represents carboxy, in the presence of a dehydrating agent such as, for example, dicyclohexylcarbodiimide.

When necessary in the preparation of compounds of Formula I separation of cis/trans isomers or intermediates or final products can be carried out by chromatographic techniques.

The compounds of Formula I contain at least one asymmetrical carbon atom and therefore exist as stereoisomers. Methods of separating the stereoisomers of a particular compound will be apparent to those skilled in the art. For example, when $R_1$ is hydrogen, the individual optical isomers of the compounds of Formula I wherein $R_a$ and $R_b$ are hydrogen and $R_c$ is hydrogen, carboxy or alkoxycarbonyl may be separated in manner known per se using optically active acids or bases. In particular, the amino group distal to the fluorinated methyl group can be protected using a ($C_2$-$C_5$ alkoxycarbonyl) phthalimide in a solvent such as, for example tetrahydrofuran, diethyl ether or $C_1$-$C_4$ alkanol, e.g. as methanol or ethanol. The protected amine derivative is then resolved using a chiral acid. The resolved phthalimido compound is then deprotected using, for example, hydrazine or methylamine to remove the phthalimide group followed if required by acid or base hydrolysis to cleave the ester product to obtain the corresponding acid. The thus resolved acids, esters and amines may be employed to prepare the individual isomers of other compounds of the invention in the manner described hereinbefore.

The compounds produced by the foregoing processes may be isolated either per se or as acid addition salts thereof.

The acid addition salts are preferably the pharmaceutically acceptable, non-toxic addition salts with suitable acids such as those previously referred to in this Specification. Apart from pharmaceutically acceptable acid addition salts, other salts are also included within the scope of acid addition salts, such as for example, those with picric or oxalic acid; they may serve as intermediates in the purification of the compounds or in the preparation of other, for example, pharmaceutically acceptable, acid addition salts, or are useful for identification or characterisation of the bases.

A resulting acid addition salt may be converted into the free compound according to known methods, for example, by treating it with an alkali or alkaline earth metal hydroxide or alkoxide; with an alkali metal or an alkaline earth metal carbonate or hydrogen carbonate; with trialkylamine; or with an anion exchange resin.

A resulting acid addition salt may also be converted into another acid addition salt according to known methods; for example, a salt with an inorganic acid may be treated with a sodium, barium or silver salt of an acid in a suitable diluent, in which a resulting inorganic salt is insoluble and is thus removed from the reaction medium. An acid addition salt may also be converted into another acid addition salt by treatment with an anion exchange preparation.

The compounds of Formula I are also of use as intermediates in the preparation of arginine decarboxylase-inhibiting compounds which differ from those of Formula I in that $R_a$ represents amidino. These arginine decarboxylase-inhibiting compounds can be obtained in manner known per se from the corresponding compounds of Formula I wherein $R_a$ represents hydrogen and, when $R_b$ is hydrogen, the amino group —$NHR_b$ is protected, preferably by a phthaloyl group, by treatment with an alkylisothiouronium salt such as, for example, ethylisothiouronium bromide, in the presence of a base. Conveniently, the reactant of Formula I can be obtained by selective hydrolysis, for example heating in conc. hydrochloric acid for 5 to 15 minuts, of a derivative in which the terminal amino group (—$NHR_a$) is in the form of an urotropine salt and the other amino group (—$NHR_a$) is in the form of a phthalimido group. Said derivatives can readily be obtained from a compound of Formula II in which the said other amino group is already in the form of a phthalimido group.

Suitably, the reaction with the alkylisothiouronium salt can be carried out at a pH of 9 to 13 at about 25° C. for about 6 to 60 hours using aqueous sodium or potassium hydroxide as the base. The reacted mixture is neutralized with acid, such as, for example hydrochloric acid, and the product isolated. Alternatively, the treatment with the alkylisothiouronium salt can be conducted under anhydrous conditions in an organic solvent such as methanol.

The compounds of Formula I and the said arginine decarboxylase-inhibiting compounds may be used in combination as antibacterial agents.

The invention is illustrated by the following nonlimiting Examples. All NMR measurements are given on the delta scale (i.e. tetramethylsilane=0).

EXAMPLE I

2-Difluoromethyl-2,5-diamino-3-(E)-penten-1-oic acid (i.e. α-difluoromethyl-trans-β-dehydroornithine)

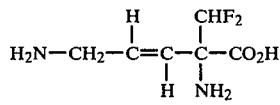

(A) Preparation of: Tert.-butyl 2-ethoxycarbonyl-4-pentenoate

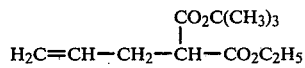

To a suspension of sodium hydride (0.16 M, 6.98 g of a 55% dispersion in oil washed three times with tetrahydrofuran) in tetrahydrofuran (200 mL) is added t-butyl ethyl malonate (30.08 g, 0.16 M). After stirring for 1 hour at room temperature (the evolution of hydrogen has at that time ceased), a solution of allyl bromide (19.36 g, 0.16 M) in tetrahydrofuran (120 mL) is rapidly added. Stirring is continued for 30 mins. The mixture is then quenched with brine, and extracted three times with diethyl ether (200 mL). The organic phase in washed with water, brine, dried over magnesium sulfate and concentrated in vacuo. The residue is distilled to give 18.6 g of tert.-butyl 2-ethoxycarbonyl-4-pentenoate (bp 50°–52° C., 0.15 mm Hg).

NMR (CDCl$_3$) ppm: 1.27 (3H, t, CH$_3$); 2.4–2.8 (2H, m, CH$_2$); 3.05–3.02 (1H, m, —CH—); 4.14 (2H, q, —OCH$_2$—); 4.8–6.1 (3H, m, CH=CH$_2$); 1.44 (9H, s, C(CH$_3$)$_3$.

(B) Preparation of: Tert.-butyl 2-ethoxycarbonyl-2-difluoromethyl-4-pentenoate

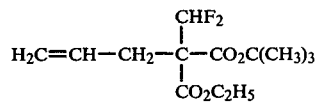

To a suspension of sodium hydride (0.08 M, 3.49 g of a 55% dispersion in oil washed three times with tetrahydrofuran) in tetrahydrofuran 90 mL) is added, at room temperature under nitrogen, a solution of tert-butyl 2-ethoxycarbonyl-4-pentenoate (18.4 g, 0.08 M) prepared as in Step A above. After stirring for one hour, a stream of chlorodifluoromethane is rapidly bubbled through the anion solution maintained at 45° C. Stirring is continued overnight at room temperature and the mixture is quenched with brine and extracted with diether ether (3×150 mL). The organic layer is dried over magnesium sulfate, and concentrated in vacuo to give 20.78 g of crude tert.-butyl 2-ethoxy-carbonyl-2-difluoromethyl-4-pentenoate which can be purified by chromatography on silica gel (eluant diether-ether/petroleum ether 5–95). bp: 43°–44° C., 0.06 mm Hg.

NMR (CCl$_4$) ppm: 1.27 (3H, t, CH$_3$); 1.47 (9H, s, C(CH$_3$)$_3$); 2.78 (2H, d, —CH$_2$—, J=7 Hz); 4.2 (2H, q, OCH$_2$—); 4.8–6.2 (3H, m, CH=CH$_2$; 6.16 (1H, t, CHF$_2$, J=53 Hz).

(C) Preparation of: Tert.-butyl-2-ethoxycarbonyl-2-difluoromethyl-5-bromo-3-(E)-pentenoate

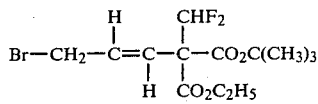

To a solution of tert.-butyl 2-difluoromethyl-2-ethoxycarbonyl-4-pentenoate (1.37, 5 mM) prepared as in Step B above in carbon tetrachloride (50 mL) is added N-bromosuccinimide (2.67 g, 15 mM) and a few crystals of benzoylperoxide. The mixture is heated at reflux temperature under light irradiation for 2 hours. After cooling, the reaction mixture is filtered and the filtrate concentrated in vacuo. The residue is chromatographed on silica gel. The mixture ether/petroleum ether (5–95) eluted tert.-butyl-2-ethoxycarbonyl-2-difluoromethyl-5-bromo-3-(E)-pentenoate.

NMR (CCl$_4$): ppm: 1.25 (3H, t, CH$_3$); 1.41(9H, s, C(CH$_3$)$_3$); 3.8–4.1 (m, CH$_2$Br); 4.16 (q, —OCH$_2$—); 5.8–6.2 (m, CH=CH); 6.0 (1H, t, CHF$_2$, J=53 Hz).

(D) Preparation of: Tert.-butyl-2-ethoxycarbonyl-2-difluoromethyl-5-phthalimido-3-(E)-pentenoate

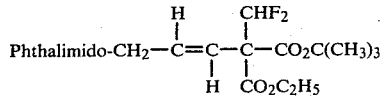

A mixture of potassium phthalimide (0.227 g, 1.23 mM), tert.-butyl-2-ethoxycarbonyl-2-difluoromethyl-5-bromo-3-(E)-pentenoate (0.44 g, 1.23 mM) prepared as in Step C above in dimethyl formamide (15 mL) is heated at 80° C. for 2 hours. The solvent is evaporated in vacuo at room temperature. The residue is extracted with methylene chloride. The organic phase is washed with water, brine, dried over magnesium sulfate, and concentrated at reduced pressure. The residue is chromatographed on silica gel. The mixture ethylacetate-cyclohexane (5:95) elutes tert.-butyl-2-ethoxycarbonyl-2-difluoro-methyl-5-phthalimido-3-(E)-pentenoate which is recrystallized in a mixture of diethyl ether and pentane: mp 77°–78° C.

NMR (CDCl$_3$): ppm 1.25 (3H, t, CH$_3$); 1.47 (9H, s, C(CH$_3$)$_3$); 4.23 (q, OCH$_2$); 4.33 (d, —CH$_2$N<); 5.83–6.23 (2H, m, —CH=CH—); 6.13 (1H, t, CHF$_2$, J=54 Hz); 7.76 (4H, m, H aromatic).

(E) Preparation of: 2-Ethoxycarbonyl-2-difluoromethyl-5-phthalimido-3-(E)-pentenoic acid

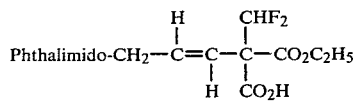

Tert.-butyl 2-ethoxycarbonyl-2-difluoromethyl-5-phthalimido-3-(E)-pentenoate (0.9 g) prepared as in Step D above is dissolved in trifluoroacetic acid (10 mL). After stirring for 1.5 hours at room temperature, the excess acid is evaporated under reduced pressure. The residue upon trituration with diethyl ether yields 0.7 g of solid 2-ethoxycarbonyl-2-difluoromethyl-5-phthalimido-3-(E)-pentenoic acid.

NMR (CDCl$_3$) ppm 1.23 (3H, t, CH$_3$); 4.05–4.6 (4H, m, >N—CH$_2$— and O—CH$_2$—), 5.9–6.1 (2H, m, —HC=CH—); 6.23 (1H, t, CHF$_2$, J=54 Hz); 7.6–8.0 (4H, m, aromatic); 8.2 (1H, s, CO$_2$H).

(F) Preparation of: 2-Ethoxycarbonyl-2-difluoromethyl-5-phthalimido-3-(E)-pentenoic acid chloride

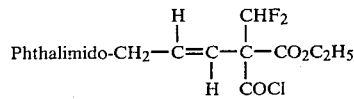

A solution of 2-ethoxycarbonyl-2-difluoromethyl-5-phthalimido-3-(E)-pentenoic acid (1.85 g; 5 mM) prepared as in Step E above in thionyl chloride (20 ml) is heated at reflux temperature for 3 hours. The excess thionyl chloride is evaporated in vacuo to yield crude 2-ethoxycarbonyl-2-difluoromethyl-5-phthalimido-3-(E)-pentenoic acid chloride as an oily residue.

(G) Preparation of: 2-Ethoxycarbonyl-2-difluoromethyl-5-phthalimido-3-(E)-pentenoic acid azide

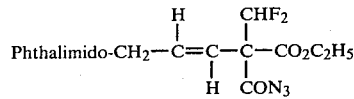

The oily residue obtained in Step F above is dissolved in acetone (15 ml), the solution cooled to 0° C., and sodium azide (0.34 g) in water (2 ml) is added dropwise. After stirring for 1 hour at room temperature, the reaction mixture is extracted with diethyl ether (3×30 ml). The organic layers are combined, washed with brine, dried over magnesium sulfate and concentrated in vacuo at room temperature to yield crude 2-ethoxycarbonyl-2-difluoromethyl-5-phthalimido-3-(E)-pentenoic acid azide (1.6 g) as an oil.

(H) Preparation of: Ethyl-2-methoxycarbonylamino-2-difluoromethyl-5-phthalimido-3-(E)-pentenoate

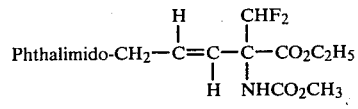

The crude acyl azide obtained in Step G is dissolved in anhydrous methanol (30 ml) and the solution heated at reflux temperature for 12 hours. The solvent is evaporated off in vacuo and the residue is chromatographed on silica gel to give on elution with ethyl acetate-petroleum ether (3:7) ethyl-2-methyloxycarbonylamino-2-difluoromethyl-5-phthalimido-3-(E)-pentenoate (1.3 g) as an oil.

NMR (CDCl$_3$) ppm: 1.23 (3H, t, CH$_2$CH$_3$); 3.6 (3H, s, OCH$_3$); 4.03-4.4 (4H, m, —CH$_2$N< and OCH$_2$); 5.56 (1H, s, —NH); 5.83-6.0 (2H, m, HC=CH); 6.17 (1H, t, J=54 Hz, CHF$_2$); 7.46-7.83 (4H, m, H aromatic).

(I) Preparation of: 2-Difluoromethyl-2,5-diamino-3-(E)-penten-1-oic acid

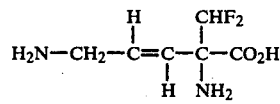

The carbamate obtained in Step H is dissolved in a mixture of acetic acid (10 ml) and concentrated hydrochloric acid (30 ml). The mixture is heated at 105° C. for 44 hours and then is concentrated in vacuo. The residue is taken up with water (10 ml) and the insoluble material is filtered off. The filtrate is concentrated at reduced pressure to give crude 2-difluoromethyl-2,5-diamino-3-(E)-pentenoic acid dihydrochloride.

NMR (D$_2$O) ppm (TMS external reference) 3.5-3.8 (2H, m, —CH$_2$—N<); 6.0-6.16; (2H, m, —CH=CH—); 6.4 (1H, t, CHF$_2$, J=52 Hz).

The dihydrochloride salt is dissolved in absolute ethanol (10 ml). Propylene oxide is added in excess to precipitate 2-difluoromethyl-2,5-diamino-3-(E)-pentenoic acid monohydrochloride (0.5 g) which is recrystallized from water ethanol.

mp: 130° C.

NMR (D$_2$O) ppm: 3.6-3.8 (2H, m, —CH$_2$—N<); 5.93-6.16 (2H, m, —CH=CH); 6.36 (1H, t, J=52 Hz, CHF$_2$).

TLC NH$_4$OH$_{conc.}$/EtOH (70/30):Rf:0.49

The monohydrochloride salt is dissolved in water (10 mmole salt per 10 ml water), aqueous triethylamine (1 equivalent) is added and the aqueous phase is concentrated under reduced pressure. The residue is washed extensively with chloroform to yield the insoluble 2-difluoromethyl-2,5-diamino-3-(E)-penten-1-oic acid.

EXAMPLE II

1-Fluoro-2,5-diamino-3-(E)-pentene, dihydrochloride
(i.e. α-fluoromethyl-trans-β-dehydroputrescine)

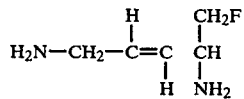

(A) Preparation of: 1-Fluoro-2-amino-3-pentene (cis/trans)

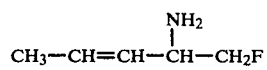

Under an atmosphere of nitrogen, propenylmagnesium bromide is prepared from 9.72 g of magnesium turnings (400 mmoles), freshly distilled 1-bromo 1-propene (cis/trans mixture, 24.2 g, 200 mmoles) and 180 ml of dry tetrahydrofuran. The colored solution is separated from the excess of magnesium and cooled to −30° C. Fluoroacetonitrile (11.8 g, 200 mmoles) in tetrahydrofuran (50 ml) is added dropwise during 20 mins and the reaction mixture is kept at −30° C. for an additional 20 mins. A solution/suspension of sodium borohydride (7.6 g, 200 mmoles) in methanol (400 ml) and water (8 ml) cooled to −50° C. is poured into the reaction mixture previously cooled to −50° C. The temperature rises to −10° C., and after cooling to −30° C. the temperature is allowed to rise to 0° C. during 1.5 hours. The mixture is acidified with 6 N hydrochloric acid, evaporated, the residue is diluted with water, extracted twice with diethyl ether to remove by-products, made alkaline with 4 N sodium hydroxide and extracted again twice with diethyl ether. After drying over sodium sulfate and filtration, dry hydrogen chloride gas is bubbled through the etheral solution. The oily precipitate formed (12 g, 43%) is dissolved in water, filtered, saturated with sodium chloride, made alkaline with 4 N sodium hydroxide and extracted twice with small portions of diethyl ether. After removing the ether at normal pressure, the black oily residue is distilled under reduced pressure (15 mm Hg) to give a colorless liquid (4.4 g, 21%, bp$_{15}$ 60°-100° C.) which is distilled again at normal pressure (some decomposition) to afford 1-fluoro-2-amino-3-pentene (cis/trans mixture, 2.8 g, 13%, bp 110°-180° C.) as a colorless oil. NMR (CDCl$_3$) ppm 1.45 (2H, s, —NH$_2$), 1.67 (3H, d of broad s, J=6 Hz), 3.83 (1H, broad m), 4.22 (2H, d of m, J$_{H-F}$=46 Hz), 5.42 (2H, broad m).

(B) Preparation of: N-1-fluoro-3-pentene-2-yl, N$^1$-ethoxycarbonyl-o-phthalamide (cis/trans)

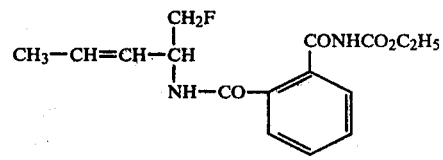

A mixture of 1-fluoro-2-amino-3-pentene (840 mg, 8.15 mmoles) prepared as in Step A above and N-ethoxycarbonylphthalimide (1.79 g, 8.15 mmoles) in 30 ml of dry benzene is kept at room temperature overnight. N-1-fluoro-3-pentene-2-yl, N'-ethoxycarbonyl-o-phthalamide precipitates as white crystals (1.26 g, 50%; cis and trans mixture).

NMR (CDCl$_3$) ppm 1.40 (3H, t, J=7 Hz), 170 and 1.73 (3H, 2d, J=6 Hz and J=8 Hz), 4.13 (2H, q, J=7 Hz), 4.43 (2H, d of m, J$_{H-F}$=48 Hz), 5.13 (1H, broad m), 5.7 (2H broad m), 6.7 (1H, m, —NH—), 7.42 (4H, s).

(C) Preparation of: 1-Fluoro-2-phthalimido-3-pentene (cis/trans)

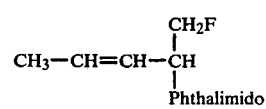

N-1-fluoro-3-pentene-2-yl, N'-ethoxycarbonyl-o-phthalimide prepared as in Step B above (1.26 g, 4.07 mmoles) is kept overnight at room temperature in 20 ml of methylene chloride in the presence of triethylamine (411 mg, 4.07 mmoles). Extraction with 1 N hydrochloric acid, then with water and evaporation affords 1-fluoro-2-phthalimido-3-pentene (cis/trans mixture, 800 mg, 84%) as an oil.

NMR (CDCl₃) ppm: 1.63 and 1.70 (3H, 2d, J=6 Hz and J=5 Hz), 3.90 to 5.57 (3H, complex multiplets), 5.70 (2H, m), 7.57 (4H, m).

(D) Preparation of: 1-Fluoro-2-phthalimido-5-bromo-3-(E)-pentene

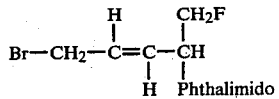

A mixture of 1-fluoro-2-phthalimido-3-pentene (800 mg, 3.4 mmoles) prepared as in Step C above, N-bromosuccinimide (612 mg. 3.4 mmoles), carbon tetrachloride (30 mL) and a few mg of benzoyl peroxide is heated under strong reflux during irradiation with a lamp (325 W) during one hour. After washing with water the organic phase is dried over magnesium sulfate and then concentrated under reduced pressure to yield 1-fluoro-2-phthalimido-5-bromo-3-pentene as a slightly yellow oil (1.06 g, quantitative yield).

NMR (CDCl₃) ppm: 3.87 (2H, m), 4.38 (1H, m), 5.15 (2H, m), 6.03 (2H, m), 7.70 (4H, m).

This NMR spectrum is identical with the NMR spectrum of 1-fluoro-2-phthalimido-5-bromo-3-(E)-pentene obtained from 1-fluoro-2-phthalimido-5-ethoxy-3-(E)-pentene by boron tribromide cleavage in Example III Step F.

(E) Preparation of: 1-Fluoro-2,3-diphthalimido-3-(E)-pentene

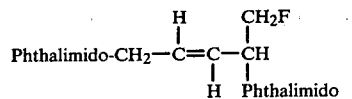

A mixture of 1-fluoro-2-phthalimido-5-bromo-3-(E)-pentene (1.06 g, 3.4 mmoles) prepared as in Step D above and potassium phthalimide (756 mg, 4.08 mmoles) is heated at 80° C. in dry, N,N-dimethylformamide (15 ml) for 2.5 hours. After cooling, water is added to the reaction mixture and the solid is filtered off. Dissolving in chloroform and extraction with 1 N potassium hydroxide to remove remaining phthalimide followed by drying the organic phase over magnesium sulfate and then concentration under reduced pressure affords 1-fluoro-2,5-diphthalimido 3-(E)-pentene as a yellowish solid (1.15 g, 85%) which is recrystallized from chloroform/petroleum ether 788 mg, 61%).

Anal. Calcd for C₂₁H₁₅O₄N₂F: C, 66.66; H, 4.00; N, 7.40. Found: C, 66.38; H, 4.11; N, 7.25.

NMR (CDCl₃) ppm: 4.28 (2H, m), 4.47 (1H, m), 5.15 (2H, m), 6.00 (2H, m), 7.72 (8H, m).

(F) Preparation of: 1-Fluoro-2,5-diamino-3-(E)-pentene, dihydrochloride (crude)

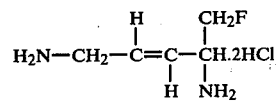

A mixture of 1-fluoro-2,5-diphthalimido-3-(E)-pentene (2.95 g, 7.8 mmoles) prepared as in Step E above and 15.6 ml of a 1 molar solution of hydrazine hydrate in ethanol is heated for 3.5 hours at 90° C. After addition of 20 ml of water and 30 ml of conc. hydrochloric acid, the mixture is heated at 90° C. for an additional hour. After cooling, the phthalhydrazide (2.35 g, 93%) is removed by filtration and the filtrate is concentrated under vacuum to give crude 1-fluoro-2,5-diamino-3-(E)-pentene, dihydrochloride as a dark colored oil (the color is partially removed after two treatments with charcoal in water).

(G) Preparation of: 1-Fluoro-2,3-di-tert.-butoxycarbonylamino-3-(E)-pentene

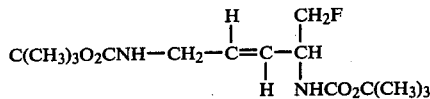

A mixture of crude 1-fluoro-2,5-diamino-3-(E)-pentene dihydrochloride (7.8 mmoles) prepared as in Step F above, di-tert.-butyl dicarbonate 3.49 g, 16 mmoles), triethylamine (1.62 g, 16 mmoles) and methylene chloride (60 ml) is stirred overnight at room temperature. After washing with water, the organic phase is dried over magnesium sulfate and then concentrated under reduced pressure to yield 1-fluoro-2,5-di-tert.-butoxycarbonylamino-3-(E)-propene as a yellowish oil (2.13 g). Rapid chormatography on silica (ethylacetate:petroleum ether 30:70) affords the pure material as a colorless oil (1.69 g, 68%).

NMR (CDCl₃) ppm: 1.42 (18H, s), 3.72 (2H, m), 4.38 (2H, d of m, J$_{H-F}$=48 Hz), 4.37 (1H, broad m), 5.12 (2H, m, 2-NHBOC), 5.68 (2H, m).

(H) Preparation of: 1-Fluoro-2,5-diamino-3-(E)-pentene

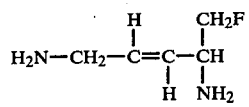

1-Fluoro-2,5-di-tert-butoxycarbonylamino-3-(E)-pentene (1.69 g, 5.3 mmoles) prepared as in Step G above is treated overnight with diethyl ether saturated with hydrogen chloride gas. The precipitate (795 mg, 78%) is filtered off, washed with diethyl ether and recrystallized from methanol/acetone to give pure 1-fluoro-2,5-diamino 3-(E)-pentene, dihydrochloride (650 mg, mp 176° C.) as white crystals.

Anal. Calcd for C₅H₁₃N₂FCl₂: C, 31.43; H, 6.86; N, 14.66. Found: C, 31.55; H, 6.72; N, 14.70.

NMR (D₂O/DCl approx 1/1) ppm: 3.73 (2H, broad d, J=6 Hz), 4.33 (1H, broad m), 4.78 (2H, d of m, J$_{H-F}$=46 Hz), 6.08 (2H, m, J=16 Hz, coupling characteristic for trans-olefin).

The dihydrochloride salt is dissolved in methanol, sodium methoxide (2 equivalents) added and the solution evaporated to dryness under reduced pressure. The residue is dissolved in absolute ethanol, filtered and the filtrate evaporated to dryness under reduced pressure to yield 1-fluoro-2,5-diamino-3-(E)-pentene as an oil.

EXAMPLE III

1-Fluoro-2,5-diamino-3-(E)-pentene, dihydrochloride
(i.e. α-fluoromethyl-trans-β-dehydroputrescine)

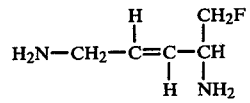

(A) Preparation of: 1,3-Dihydro-propene (cis/trans)

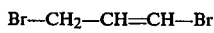

A mixture of 1-bromo-1-propene (60 g, 0.5 mole), N-bromosuccinimide (80 g, 0.45 mole), benzoyl peroxide (200 mg) and carbon tetrachloride is heated under reflux for 5 hours (250 ml under light irradiation (325 W Lamp). After cooling, succinimide is filtered off and the solvent is removed under reduced pressure at 25° C. The residue is dried over calcium chloride and distilled under reduced pressure (25 mm Hg) to afford 1,3-dibromo-propene as a colorless liquid (bp$_{25}$=65°–70° C., 62 g, 62%).

NMR (CDCl$_3$) ppm 3.98 (2H, m), 6.32 (2H, m).

(B) Preparation of: 1-Bromo-3-ethoxy-1-propene (cis/trans)

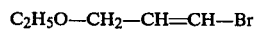

A freshly prepared solution of sodium ethoxide in dry ethanol (6.9 g Na, 0.3 mole, 100 ml EtOH) is added under nitrogen to 1,3-dibromopropene (55 g, 0.275 mole) prepared as in Step A above in 20 ml of dry ethanol. After 1.5 hours at room temperature, 100 ml of water is added to the reaction mixture, the oil formed is extracted twice with small portions of petroleum ether and dried over magnesium sulfate. Distillation at normal pressure affords 1-bromo-3-ethoxy-1-propene (bp 144°–145° C., 32.9 g, 73%).

NMR (CDCl$_3$) ppm 1.17 (3H, t, J=7 Hz), 3.42 and 3.45 (2H, 2q, J=7 Hz and J=7 Hz), 3.98 (2H, m), 6.18 (2H, m).

(C) Preparation of: 1-Fluoro-2-amino-5-ethoxy-3-pentene (cis/trans)

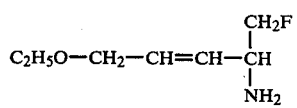

Under an atmosphere of nitrogen, 3-ethoxy-1-propen-1-yl-magnesium bromide is prepared from 8.25 g of 1-bromo-3-ethoxy-1-propene (50 mmoles) prepared as in Step B above, 12.15 g of magnesium turnings (500 mmoles) and 50 ml of dry tetrahydrofuran. After 4 hours the Grignard solution (yield according to titration: 80%) is transferred into another flask via a syringe, cooled to −30° C. and fluoroacetonitrile (2.36 g, 40 mmoles) in tetrahydrofuran (30 ml) is added dropwise during 15 mins. After 15 additional minutes at −30° C., a solution/suspension of sodium borohydride (1.52 g, 40 mmoles) in methanol (100 ml) and water (2 ml) cooled to −50° C. is poured into the reaction mixture previously cooled to −50° C. The temperature rises up to −30° C., and after stirring for 20 mins. at −20° C., the mixture is allowed to warm up to 0° C. during 1 hour. After acidifying with 6 N hydrochloric acid and evaporation, the residue is extracted twice with diethyl ether to remove by-products, made alkaline with 4 N sodium hydroxide and extracted twice with diethyl ether. Evaporation of the solvent affords crude 1-fluoro-2-amino-5-ethoxy-3-pentene (cis/trans) as a colored oil (1.0 g, 17%, based on the Grignard).

NMR (CDCl$_3$) ppm 1.18 (3H, t, J=7 Hz), 2.10 (2H, broad s, —NH$_2$), 2.98 (1H, broad m), 3.47 (2H, q, J=7 Hz), 3.97 (3H, m), 4.68 (1H, m), 5.62 (2H, m).

(D) Preparation of: N-1-fluoro-5-ethoxy-3-pentene-2-yl, N$^1$-ethoxycarbonyl-o-phthalamide

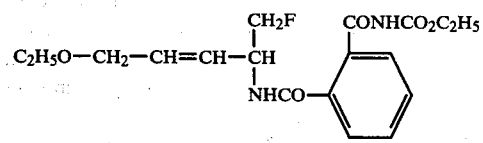

A mixture of 1-fluoro-2-amino-5-ethoxy-3-propene (1 g, 6.8 mmoles) prepared as in Step C above, N-ethoxycarbonylphthalimide (1.49 g, 6.8 mmoles) and 25 ml of dry benzene is kept over night at room temperature. The N-1-fluoro-5-ethoxy-3-pentene-2-yl, N$^1$-ethoxycarbonyl-o-phthalamide is isolated by evaporation of the solvent as an oily yellow residue and is used for the following Step E, without purification.

(E) Preparation of: 1-Fluoro-2-phthalimido-5-ethoxy-3-pentene (cis/trans) and separation of cis and trans isomers

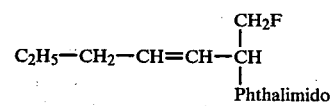

Treatment of N-1-fluoro-5-ethoxy-3-pentene-2-yl,N$^\prime$-ethoxycarbonyl-o-phthalamide prepared as in Step D above with triethylamine (687 mg, 6.8 mmoles) in methylene chloride for 5 hours at room temperature followed by 2 extractions with 1 N hydrochloride acid and evaporation gives crude 1-fluoro-2-phthalimido-5-ethoxy-3-pentene, cis/trans, 1.55 g) as a yellow oil.

Rapid chromatography on silica (ethyl acetate:petroleum ether 15:85) gives three fractions: A (150 mg), a mixed fraction B (385 mg) and fraction C (320 mg), A and C representing respectively pure cis-1-fluoro-2-phthalimido-5-ethoxy-3-pentene and trans-1-fluoro-2-phthalimido-5-ethoxy-3-pentene.

Cis-1-fluoro-2-phthalimido-5-ethoxy-3-pentene

NMR (CDCl$_3$) ppm 1.17 (3H, t, J=7 Hz), 3.47 (2H, q, J=7 Hz), 4.08 (2H, m), 4.22 to 5.65 (3H, complex multiplets), 5.83 (2H, m, J=11 Hz, coupling constant characteristics for cis-olefins), 7.62 (4H, m).

IR (film) $\nu$ cm$^{-1}$: 1780, 1720, 1620, no CH out of plane deformation near 970-960 cm$^{-1}$ (characteristic for cis-olefins).

Trans-1-fluoro-2-phthalimido-5-ethoxy-3-pentene

NMR (CDCl$_3$) ppm 1.16 (3H, t, J=7 Hz), 3.43 (2H, q, J=7 Hz), 3.92 (2H, m), 4.22 to 5.52 (3H, complex multiplets), 5.92 (2H, m, J=15 Hz, coupling constant characteristic for trans-olefins), 7.67 (4H, m).

IR (film) $\nu$ cm$^{-1}$: 1780, 1720, 1620, 975 (characteristic for the out-of-plane deformation of a trans double bond).

Total yield of the transformation of the amine to the phthalimide derivative: 45%.

(F) Preparation of: 1-Fluoro-2-phthalimido-5-bromo-3-(E)-pentene

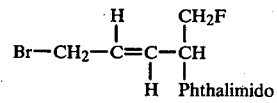

Boron tribromide (106 mg, 0.42 mmoles) in 5 ml of dry methylene chloride is added slowly to a solution of 1-fluoro-2-phthalimido-5-ethoxy-3-(E)-propene (i.e. trans), (320 mg, 1.15 mmoles) prepared as in Step E above in 10 ml of dry methylene chloride cooled at −78° C. The temperature is allowed to rise to room temperature overnight, the solvent is evaporated, and 1-fluoro-2-phthalimido-5-bromo-3-(E)-pentene (345 mg, 95%) is obtained as an oil.

NMR (CDCl$_3$) ppm 3.87 (2H, m), 4.38 (1H, m), 5.15 (2H, m), 6.03 (2H, m), 7.70 (4H, m).

This NMR spectrum is identical with the NMR spectrum of the bromo derivative obtained by the allylic bromination of the cis and trans mixture of 1-fluoro-2-phthalimido-3-pentene in Example II Step D.

(G) Preparation of: 1-Fluoro-2,5-diphthalimido-3-(E)-pentene

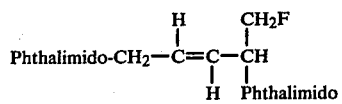

A mixture of 1-fluoro-2-phthalimido-5-bromo-3-(E)-pentene (345 mg, 1.10 mmole) prepared as in Step F above and potassium phthalimide (245 mg, 1.32 mmole) is heated at 80° C. in dry N,N-dimethylformamide (5 ml) for 2.5 hours. After cooling, water is added to the reaction mixture and the solid is filtered off. Chloroform/1 N potassium hydroxide extraction to remove the excess of phthalimide, drying, filtration and evaporation of the solvent afford 1-fluoro-2,5-diphthalimido-3-(E)-pentene as a nearly white solid (320 mg, 83%).

NMR: the spectrum is superimposable with the spectrum of the product obtained in Example II, Step E.

(H) Preparation of: 1-Fluoro-2,5-diamino-3-(E)-pentene

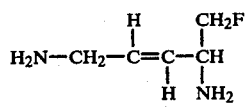

1-Fluoro-2,5-diphthalimido-3-(E)-pentene (10.5 g; 27.7 moles) prepared as in Step G above is heated at 95° C. in concentrated hydrochloric acid (250 ml) and acetic acid (100 ml) during 24 hours. After evaporation of the solvent, the brownish residue is taken up in water and phthalic acid is filtered off. The filtrate is evaporated and the solid residue is crystallized from methanol-acetone to give 1-fluoro-2,5-diamino-3-(E)-pentene, dihydrochloride (4.2 g; 79%). The free base is obtained from the dihydrochloride by the same method as that employed in Example II.

EXAMPLE IV

2-Fluoromethyl-2,5-diamino-3-(E)-penten-1-oic acid, monohydrochloride (i.e. α-fluoromethyl-β-trans-dehydroornithine

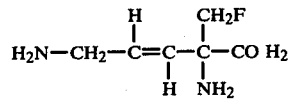

(A) Preparation of: 2-Fluoromethyl-2-amino-3-pentenenitrile(cis/trans)

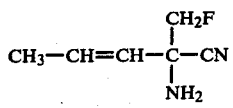

Under an atmosphere of nitrogen, propenylmagnesium bromide is prepared from magnesium turnings (9.8 g, 400 mmoles), freshly distilled 1-bromo-1-propene (24.2 g, 200 mmoles) and 200 mL of dry tetrahydrofuran. After removing the Grignard solution from the excess of magnesium and cooling to −40° C., fluoroacetonitrile (11.8 g, 200 mmoles) in tetrahydrofuran (70 mL) is added during 15 mins. The reaction mixture is then poured into a solution of sodium cyanide (40 g) and ammonium chloride (59 g) in water (400 mL) and kept 1 hour at room temperature. After saturation with sodium chloride, the tetrahydrofuran layer is separated and evaporated under reduced pressure. The residue is dissolved in diethyl ether, washed with water, dried with sodium sulfate and evaporated to give crude 2-fluoromethyl-2-amino-3-pentenenitrile (1:1 cis/trans mixture, 21.5 g, 84%) as a dark coloured oil which is used for the next step without further purification.

NMR (CDCl$_3$) ppm cis:*1.97 (3H, d of narrow d, J=7 Hz, J$_{allyl}$≈2 Hz); 2.20 (—NH$_2$, broad s), 4.32 (2H, d of AB, J$_{AB}$=8.5 Hz, J$_{H-F}$=46 Hz), 5.12 (1H, center of A part of ABX$_3$, J$_{AB}$=12 Hz, additional allylic couling), 5.82 (1H, center of B part of ABX$_3$, 2q, J$_{AB}$=12 Hz, J$_{BX}$=7 Hz).

*Assignment of signals is possible by partial separation of the isomers by liquid-liquid partition (water/diethyl ether).

trans:*1.77 (3H, d of narrow d, J=7 Hz, J$_{allyl}$≈1 Hz), 2.20 (—NH$_2$, broad s), 4.25 (2H, d, J$_{HF}$=46 Hz), 5.27 (1H, center of A part of ABX$_3$, J$_{AB}$=15 Hz, additional allylic coupling), 6.13 (1H, center of B part of ABX$_3$, 2q, J$_{AB}$=15 Hz, J$_{BX}$=7 Hz).

(B) Preparation of: 2-Fluoromethyl-2-trifluoroacetamido-3-pentenenitrile

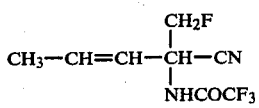

2-Fluoromethyl-2-amino-3-pentenenitrile (21.5 g, 168 mmoles) prepared as in Step A above dissolved in methylene chloride (300 mL) is cooled to −30° C. and treated with trifluoroacetic anhydride (34.8 g, 166 mmoles). The mixture is allowed to warm up to room temperature overnight and the solvent is removed under reduced pressure. Dissolving the residue in ethyl acetate, washing with water, drying with sodium sulfate and evaporation gives a dark oil (35 g). TLC ethyl acetate/petroleum ether 40:60) indicates two major spots with Rf 0.65 and 0.60 corresponding respectively to the cis and trans isomers of 2-fluoromethyl-2-trifluoroacetamido-3-pentenenitrile.

Rapid chromatography and collection of the fractions corresponding to these Rf values gave 2-fluoromethyl-2-trifluoroacetamido-3-pentenenitrile. (2, 1:1 cis/trans mixture, 23.5 g, 62%) as a slightly yellow oil.

NMR (CDCl$_3$) ppm cis:**1.93 (3H, d, J−7 Hz, small allylic coupling), 4.68 (2H, d, J$_{H-F}$=46 Hz), 5.37 (1H, center of A part of ABX$_3$, J$_{AB}$=12 Hz, additional allylic coupling), 6.00

(1H, center of B part of ABX₃, 2q, $J_{AB}=12$ Hz, $J_{BX}=7$ Hz), 7.6 (NH, broad s).

**A small amount of cis/trans mixture is partially separated into the isomers by chromatography.

trans:**1.82 (3H, d, J=7 Hz, small allylic coupling), 4.62 (2H, d, $J_{H-F}=46$ Hz), 5.40 (1H, center of A part of ABX₃, $J_{AB}=15$ Hz, additional allylic coupling), 6.27 (1H, center of B part of ABX₃, 2q, $J_{AB}=15$ Hz, $J_{BX}=7$ Hz), 7.6 (NH, broad s).

(C) Preparation of: 2-Fluoromethyl-2-trifluoroacetamido-5-bromo-3-(E)-pentenenitrile

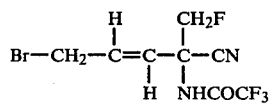

A mixture of 2-fluoromethyl-2-trifluoroacetamido-3-pentenenitrile, (23.5 g, 105 mmoles) prepared as in Step B above, N-bromosuccinimide (19 g, 107 mmoles), carbon tetrachloride (160 mL), and benzoylperoxide is irradiated and heated under reflux by means of a 325 W lamp for 30 mins. During this time, succinimide separates together with an oil which are both collected by filtration on a fritted glass. Dissolving in chloroform, removal of succinimide by filtration and evaporation gives crude 2-fluoromethyl-2-trifluoroacetamido-5-bromo-3-(E)-pentenenitrile (31 g, 97%) as a brown oil which is used for the next step without further purification.

NMR (CDCl₃) ppm 2.75 (succinimide), 3.97 (2H, d, J=7 Hz), 4.68 (2H, d, $J_{H-F}=46$ Hz), 5.73 (1H, center of A part of ABX₂, $J_{AB}=15$ Hz), 6.43 (1H, center of B part of ABX₂, 2t, $J_{AB}=15$ Hz, $J_{BX}=7$ Hz), 7.75 (NH, broad s).

(D) Preparation of: 2-Fluoromethyl-2-trifluoroacetamido-5-hexamethylene tetrammonium-3-(E)-pentenenitrile bromide

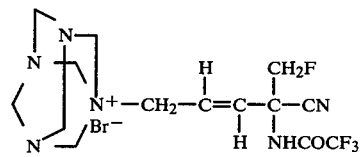

To a solution of 2-fluoromethyl-2-trifluoroacetamido-5-bromo-3-(E)-pentenenitrile (15.0 g, 49.5 mmoles) prepared as in Step C above in chloroform (40 mL) is added hexamethylenetetramine (6.93 g, 49.5 mmoles) in 80 mL of chloroform. A brown oil separates which solidifies on standing overnight. The crude product (14.7 g, 67%) is recrystallized by dissolving in hot methanol and addition of twice the volume of chloroform to give pure 2-fluoromethyl-2-trifluoroacetamido-5-hexamethylenetetrammonium-3-(E)-pentenenitrile bromide (4, 11.3 g, 52%) as heavy colourless crystals containing 1 mole of chloroform; mp 147° C.

NMR (CD₃OD) ppm 3.50 (2H, broad d, J=6-7 Hz), 4.43 (6H, s), 4.63 (2H, d, $J_{H-F}=76$ Hz), 4.95 (6H, s), 6.07 (2H, m), 7.58 (1H, C$\underline{H}$Cl₃, s).

Anal. Calcd for C₁₅H₂₀BrCl₃F₄N₆O: C, 32.02; H, 3.58; N, 14.94. found: C, 32.00;

(E) Preparation of: 2-Fluoromethyl-2,5-diamino-3-(E)-penten-1-oic acid,

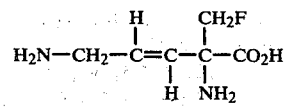

2-Fluoromethyl-2-trifluoroacetamido-5-hexamethylene-tetrammonium-3-(E)-pentenenitrile bromide (5.62 g, 10 mmoles) prepared as in Step D above is dissolved in conc. hydrochloric acid (100 mL) and evaporated to dryness at 35° C. under reduced pressure. This operation is repeated twice more. The residue is heated with conc. hydrochloric acid (100 mL) at 100° C. overnight (16 hours) whilst a slow stream of nitrogen is passed through the solution. After evaporating the dark coloured reaction mixture under reduced pressure and drying for several hours with an oil pump, the residue is dissolved in dry ethanol (50 mL), ammonium chloride is removed by filtration and propylene oxide (1.8 g) is added to precipitate the crude monohydrochloride. After standing at 5° C. overnight, a brown, hygroscopic precipitate is collected on a fritted glass, washed with a small amount of dry ethanol, dissolved in water and treated with charcoal at 40°-50° C. for 2 hrs. Evaporation of the colourless filtrate gives a white solid which is recrystallized to give pure 2-fluoromethyl-2,5-diamino-3-(E)-penten-1-oic acid, monohydrochloride (730 mg, 36%) as colourless crystals, mp 176° C. (dec).

NMR (D₂O/DCl) ppm 3.38 (2H, broad d), 4.87 (1H center of part of ABX, $J_{AB}=11$ Hz, $J_{AX}=J_{H-F}=47$ Hz), 5.23 (1H, center of B part of ABX, $J_{AB}=11$ Hz, $J_{BX}=J_{H-F}=45$ Hz), 6.18 (2H, m).

Anal. Calcd for C₆H₁₂ClFN₂O₂: C, 36.28; H, 6.09; N, 14.10. found: C, 36.10; H, 5.88; N, 13.85.

The free diaminopentenoic acid is obtained from the hydrochloric salt by the same method disclosed in Example I in connection with the difluoromethyl analogue.

EXAMPLE V 2,2-Difluoro-2,5-diamino-3-(E)-pentene

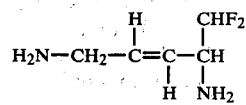

(A) Preparation of: Ethyl 2-ethoxycarbonyl-2-difluoromethyl-3-pentenoate

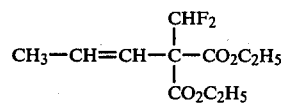

To a suspension of sodium hydride (5.5 mM, 0.264 g of a 55% dispersion in oil washed three times with pentane) in tetrahydrofuran (8 mL) is added under nitrogen a solution of diethyl propenyl malonate (1 g, 5 mM) (prepared by refluxing propionaldehyde and diethylmalonate in acetic anhydride) in tetrahydrofuran (2 mL). The reaction mixture is stirred for 14 hours at 45° C. and then a stream of chlorodifluoromethane is rapidly bubbled through the anion solution. After stirring for 7 hours, the mixture is quenched with brine and extracted with diethyl ether (3×20 mL). The organic phase is washed with brine, dried over magnesium sulfate and concentrated in vacuo. The residue is distilled to give the expected ethyl 2-ethoxycarbonyl-2-difluoromethyl-3-pentenoate (bp 150° C., 10 mm Hg).

RMN (CDCl): ppm 1.25 (6H, t, CH₃); 1.7–1.87 (3H, m, CH₃-C); 4.2 (4H, 2, —OCH₂—); 5.6–5.8 (2H, m, CH=CH); 6.08 (1H, t, CHF₂, J=54 Hz).

(B) Preparation of: Ethyl 2-ethoxycarbonyl-2-difluoromethyl-5-bromo-3-(E)-pentenoate

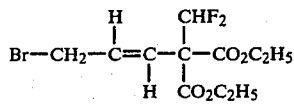

To a solution of ethyl 2-ethoxycarbonyl-2-difluoromethyl-3-pentenoate prepared as in Step A (1.82 g, 7.3 mM) in carbon tetrachloride (60 mL) is added N-bromo-succinimide (1.3 g or 7.3 mM) and a few crystals of benzoylperoxide. The mixture is heated at reflux temperature under light irradiation for 1.5 hours. After cooling, the reaction mixture is filtered and the filtrate concentrated in vacuo to give ethyl 2-ethoxycarbonyl-2-difluoromethyl-5-bromo-3-(E)-pentenoate.

RMN (CDCl₃): ppm 1.3 (6H, t, OCH₂CH₃); 3.9–4.25 (6H, m, OCH₂— and BrCH₂), 5.85–6.15 (2H, m, HC=CH), 6.25, (1H, t, J=54 Hz, CHF₂).

(C) Preparation of: Ethyl 2 ethoxycarbonyl-2-difluoromethyl-5-hexamethylene-tetrammonium-3-(E)-pentenoate hydrobromide

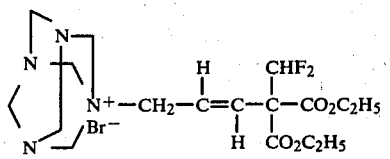

To a solution of ethyl 2-ethoxycarbonyl-2-difluoromethyl-5-bromo-3-(E)-pentenoate prepared as in Step B (3.29 g or 10 mM) in chloroform (15 mL) is added hexamethylenetetramine (1.4 g or 10 mM) in chloroform (15 mL). The solid which separates on standing is separated by filtration. Recrystallization in ethanol-chloroform yields ethyl-2-ethoxycarbonyl-2-difluoromethyl-5-hexamethylenetetrammonium-3-(E)-pentenoate hydrobromide (2.1 g).

(D) Preparation of: 2-Difluoromethyl-5-amino-3-(E)-penten-1-oic acid hydrochloride

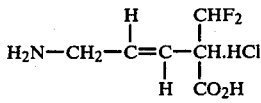

Ethyl 2-ethoxycarbonyl-2-difluoromethyl-5-hexamethylenetetraammonium-3-(E)-pentenoate hydrobromide prepared as in Step C (1.5 g) is dissolved in concentrated hydrochloric acid. The solution is concentrated at reduced pressure at 30° C. This operation is repeated three times. The residue is then dissolved in concentrated hydrochloric acid (20 mL) and the reaction mixture is heated at reflux temperature for 24 hours, while a slow stream of nitrogen is passed through the solution. The residue obtained upon concentration in vacuo is triturated with absolute ethanol (20 mL). The insoluble material is filtered and the filtrate treated with charcoal. Evaporation of the solvent yields crude 2-difluoromethyl-5-amino-3-(E)-penten-1-oic acid hydrochloride.

(E) Preparation of: 2-Difluoromethyl-5-phthalimido-3-(E)-penten-1-oic acid

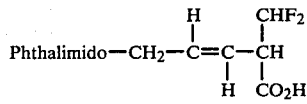

The procedures of steps B and C of Example II are substantially repeated commencing with 2-difluoromethyl-5-amino-3-(E)-penten-1-oic acid hydrochloride prepared as in step D above to yield 2-difluoromethyl-5-phthalimido-3-(E)-penten-1-oic acid. Alternatively, tert. butyl-2-tert-butyloxycarbonyl-2-difluoromethyl-5-phthalimido-3-(E)-pentanoate (1 g) prepared as described in Steps A to D of Example I using di-tert-butyl malonate is dissolved at 0° C. in trifluoroacetic acid (10 ml). The temperature is allowed to rise to 25° C. over 2.5 hours and the reacted mixture evaporated under reduced pressure. The residue is dissolved in acetic acid (30 ml), the mixture stirred overnight and then concentrated under reduced pressure. The residue is recrystalized to yield 2-difluoromethyl-5-phthalimido-3-(E)-pentene-1-oic acid.

NMR (CDCl₃+CD₃OD) ppm 4.28 (2H, m, CH₂+N), 5.93 (1H, d of t, 1H CHF₂), 5.6–5.9 (2H, m, CH=CH), 7.73 (4H, m, H aromatic).

(F) 2,2-Difluoro-2,5-diamino-3-(E)-pentene

The procedure of Steps F, G, H and I of Example I are substantially repeated commencing with 2-difluoromethyl-5-phthalimido-3-(E)-penten-1-oic acid prepared as in Step E above to yield 2,2-difluoro-2,5-diamino-3-(E)-pentene dihydrochloride.

NMR (D₂O; external reference TMS) ppm 3.66 (2H, d, J$_{AB}$=5 Hz, CH₂NH₂); 6.13 (1H, d of t, J$_{HF}$=53 Hz, J$_{HH}$=2.7 Hz); 5.9–6.20 (2H, m, CH=CH).

EXAMPLE VI

2-Difluoromethyl-2,5-diamino-3-(E)-penten-1-oic acid

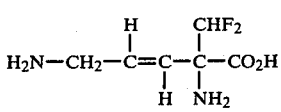

(A) Preparation of: Ethyl 2-difluoromethyl-2-chlorocarbonyl-4-pentenoate

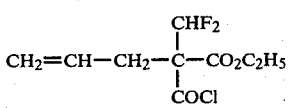

The procedures of Steps E and F of Example I are substantially repeated commencing with tert-butyl 2-ethoxycarbonyl-2-difluoromethyl-4-pentenoate prepared as in Step B of Example I to yield ethyl 2-difluoromethyl-2-chlorocarbonyl-4-pentenoate.

(B) Preparation of: Ethyl 2-carbamoyl-2-difluoromethyl-4-pentenoate

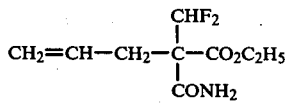

To a solution of ethyl 2-difluoromethyl-2-chlorocarbonyl-4-pentenoate prepared as in Step A above (3.16 g) in acetone (25 mL) is added ammonium acetate (3.16 g). The mixture is stirred at room temperature for 3 hours. The insoluble material is filtered and the filtrate concentrated at reduced pressure. The residue is dissolved in ether (50 mL). The organic phase is washed with water, brine and dried over magnesium sulfate to give ethyl 2-carbamoyl-2-difluoromethyl-4-pentenoate (2.65 g) as an oil.

NMR (CCl$_4$) ppm: 1.26 (3H, t, CH$_3$); 2.7 (2H, d, —CH$_2$—); 4.13 (2H, 2, —OCH$_2$—); 4.8–6.0 (3H, CH=CH$_2$); 6.0 (1H, t, CHF$_2$, J=54 Hz); 7.0 (2H, broad s, NH$_2$).

(C) Preparation of: Ethyl 2-amino-2-difluoromethyl-4-pentenoate

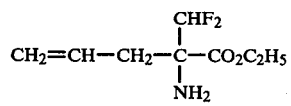

A solution of ethyl 2-carbamoyl-2-difluoromethyl-4-pentenoate prepared as in Step B (2.3 g) and iodo-benzene ditrifluoroacetate (3.5 g) in acetonitrile (14 mL) and water (14 mL) is stirred at 80° C. for 16 hours. Water (20 mL) is added and the mixture is extracted with ether (3×20 mL). The aqueous phase is concentrated and the residue suspended in saturated aqueous sodium bicarbonate (10 mL). The suspension is extracted with diethyl ether (3×20 mL). The organic layers are combined, washed with brine, dried over magnesium sulfate and concentrated in vacuo to give ethyl 2-amino-2-difluoromethyl-4-pentenoate (0.6 g) as an oil.

NMR (CCl$_4$) ppm: 1.17 (3H, t, CH$_3$); 1.73 (2H, broad s, NH$_2$); 1.95–2.61 (2H, m, —CH$_2$—); 4.06 (2H, q, —OCH$_2$—); 4.75–5.8 (3H, m, CH=CH$_2$); 5.6 (1H, t, CHF$_2$, J=55 Hz).

(D) Preparation of: Ethyl 2-difluoromethyl-2-trifluoroacetamido-4-pentenoate

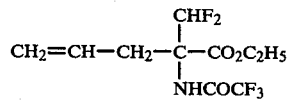

To a solution of ethyl 2-difluoromethyl-2-amino-4-pentenoate prepared as in Step C (0.45 g) in methylene chloride (5 mL) cooled to −30° C. is added trifluoroacetic anhydride (0.32 mL, 1 equiv.). The temperature of the reaction mixture is allowed to raise to room temperature and stirring is continued for 16 hours. The solvent is evaporated at reduced pressure. The residue is dissolved in ether (10 mL). The organic layer is washed with brine, dried over magnesium sulfate and concentrated in vacuo to give 2-difluoromethyl-2-trifluoroacetamido-4-pentenoate (0.5 g) as an oil.

NMR (CCl$_4$) ppm: 1.24 (3H, t, CH$_3$); 2.4–3.6 (2H, m, —CH$_2$—); 4.27 (2H, q, OCH$_2$); 4.9–5.8 (3H, m, CH=CH$_2$); 6.2 (1H, t, CHF$_2$, J=54 Hz); 7.2 (1H, broad s, NH—).

(E) Preparation of: 2-Difluoromethyl-2,5-diamino-3-(E)-penten-1-oic acid

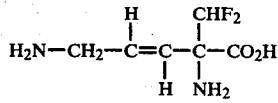

The procedures of Steps C, D and I of Example I are repeated commencing with ethyl 2-difluoromethyl-2-trifluoroacetamido-4-pentenoate prepared as described in Step D above to yield 2-difluoromethyl-2,5-diamino-3-(E)-penten-1-oic acid.

The following Examples relating to pharmaceutical compositions, the term "active compound" is used to indicate the compound 2-difluoromethyl-2,5-diamino-3-(E)-penten-1-oic acid. This compound may be replaced in these compositions by any other compound of the invention, for example by 1-fluoromethyl-2,5-diamino-3-(E)-pentene. Adjustments in the amount of medicament may be necessary or desirable depending upon the degree of activity of the medicament as is well known in the art.

EXAMPLE VII

An illustrative composition for hard gelatin capsules is as follows:

| | |
|---|---|
| (a) active compound | 20 mg |
| (b) talc | 5 mg |
| (c) lactose | 90 mg |

The formulation is prepared by passing the dry powders of (a) and (b) through a fine mesh screen and mixing them well. The powder is then filled into hard gelatine capsules at a net fill of 115 mg per capsule.

EXAMPLE VIII

An illustrative composition for tablets is as follows:

| | |
|---|---|
| (a) active compound | 20 mg |
| (b) starch | 43 mg |
| (c) lactose | 45 mg |
| (d) magnesium stearate | 2 mg |

The granulation obtained upon mixing the lactose with the compound (a) and the part of the starch and granulated with starch paste is dried, screened, and mixed with the magnesium stearate. The mixture is compressed into tablets weighing 110 mg each.

EXAMPLE IX

An illustrative composition for an injectable suspension is the following 1 ml ampul for an intramuscular injection:

| | weight percent |
|---|---|
| (a) active compound | 1.0 |
| (b) polyvinylpyrrolidone | 0.5 |
| (c) lecithin | 0.25 |
| (d) water for injection to make | 100.0 |

The materials (a)-(d) are mixed, homogenized, and filled into 1 ml ampuls which are sealed and autoclaved 20 minutes at 121° C. Each ampul contains 10 mg per ml of novel compound (a).

EXAMPLE X

| | mg/suppository |
|---|---|
| Active Compound | 50 |
| Oil of Theobroma | 950 |

The medicament is powdered and passed through a B.S. No. 100 sieve and triturated with molten oil of Theobroma at 45° C. to form a smooth suspension. The mixture is well stirred and poured into moulds each of nominal 1 G capacity, to produce suppositories.

EXAMPLE XI

The ODC inhibitory activity of the compounds of Formula I can be demonstrated in vivo according to the following procedure:

Male rats of the Sprague-Dawley strain (200–220 g body weight), purchased from Charles River, are given food and water ad libitum under a constant 12 hr light-—12 hr dark lighting schedule. Drugs are injected intraperitoneally (dissolved in 0.9% saline) or are given by gavage (dissolved in water). Rats given saline or water serve as control. Five to six hours after drug administration, the animals are killed by decapitation and the ventral prostrate and thymus are excised rapidly and immediately processed. The tissues are homogenized with three volumes of 30 mM sodium phosphate buffer (pH 7.1) containing 0.1 mM EDTA, 0.25 M sucrose, 0.1 mM pyridoxal phosphate and 5 mM dithiothreitol. Ornithine decarboxylase activities are determined on a 1000 g supernatant of prostate homogenate and on a whole thymus homogenate, essentially as described by Ono et al. (Biochem. Biophys. Acta, 284, 285 (1972)).

When tested according to the above-described procedure, representative compounds of Formula I gave the results shown in Table II below and in which the following abbreviations are used:

TABLE II

| | ODC ACTIVITY | | | |
|---|---|---|---|---|
| | VENTRAL PROSTATE | | (% CONTROL) THYMUS | |
| INHIBITORS | I.P. | GAVAGE | I.P. | GAVAGE |
| MFMDO 50 mg/kg | 18 | 36 | 50 | 54 |
| DFMDO 50 mg/kg | — | 119 | — | 87 |
| MFMDP 25 mg/kg | — | 12 | 24 | — |

MFMDO = α-fluoromethyl-trans-β-dehydro-ornithine;
DFMDO = α-difluoromethyl-trans-β-dehydro-orithine;
MFMDP = α-fluoromethyl-trans-β-dehydro-putrescine.

EXAMPLE XII

The activity of the compounds of Formula I as inhibitors of ornithine decarboxylase (ODC) can be demonstrated in vitro according to the following procedure:

Ornithine decarboxylase (ODC) is prepared from the livers of rats which have been injected with thioacetamide (150 mg/kg of body weight) 18 hrs before sacrifice, and is purified about ten fold by acid treatment at pH 4.6 as described by Ono et al. (Biochem. Biophys. Acta 284, 285 (1972)). The stock solution of ODC is comprised of protein (16 mg/mL), sodium phosphate buffer (30 mM, pH 7.1), dithiothreitol (5 mM) and pyridoxal phosphate (0.1 mM). The specific activity of this stock solution is 0.12 nmol of $CO_2$/min per mg of protein. For a typical experiment 320 μl of this stock solution are mixed at time 0 with 80 μl of a solution of the inhibitor in water and incubated at 37°. At different times 50 μl aliquots are transferred into a 1-mL assay medium containing sodium phosphate (30 mM, pH 7.1), dithiothreitol (5 mM), pyridoxal phosphate (0.1 mM), L-ornithine (0.081 mol), and DL-[1-$^{14}$C] ornithine (0.043 mol, 58 Ci/mol, Amersham) in a closed vessel in which a filter paper moistered with 50 μl hyamine hydroxide (1 M) is fitted. The reaction is allowed to proceed for 60 min at 37° C. and then terminated by addition of 0.5 ml of 40% trichloroacetic acid. After an additional 30 min the $CO_2$ absorbed on the filter paper is counted in a standard scintillation cocktail. $K_I$ (apparent dissociation constant) and $\tau_{50}$ (half-life, at infinite concentration of inhibitor are calculated according to the method of Kitz and Wilson (J. Biol. Chem., 237, 3245 (1962)).

When tested according to the above-described procedure, representative compounds of Formula I gave the results shown in Table III below. The same abbreviations are used as in Table II and DFMDP is α-difluoromethyl-trans-β-dehydroputrescine. Half-life ($t_{1/2}$) at 10 M is also set forth in Table III.

TABLE III

| | ODC | | |
|---|---|---|---|
| | $K_I$ (μM) | 50 (Min.) | $t_{\frac{1}{2}}$ (Min.) |
| MFMDO | 2.8 | 2.7 | 3.1 |
| DFMDO | 30.0 | 2.5 | 10.0 |
| MFMDP | 42 | 0.2 | 0.9 |
| DFMDP | 60 | 0.7 | 5 |

EXAMPLE XIII

The anti-neoplastic effects of the compounds of Formula I can be demonstrated in vivo in C57BL (BD2F) mice inoculated i.p. with L 1210 leukemia ($10^6$ cells) or in BALBC mice inoculated s.c. with EMT6 solid sarcona ($10^5$ cells).

When tested in mice against L 1210 leukemia and EMT6 solid tumors, -fluoromethyl-trans-dehydroputrescine (MFMDP) gave the following results:

(A) L 1210 Leukemia 0.2% MFMDP in water as sole drinking fluid from day 1 after inoculation and maintained thereafter, did not prolong the survival of the mice. When injected i.p. (twice a day from day 1) at a dose of 50 mg/kg it increased by 20% the mean survival time of the mice. At a dose of 200 mg/kg i.p., the compound was toxic and no increased survival could be observed.

(B) Solid EMT6 sarcoma

2% MFMDP in water as sole drinking fluid starting 4 days after inoculation of the cells, inhibited by 60% to 70% the growth of the tumor at day 17. When given at 0.2% in water, it inhibited by 25% tumor growth. When injected i.p., 200 mg/kg twice a day starting 4 days after inoculation, the compound inhibited by 50% tumor growth at day 13. ODC activity in the tumor was markedly inhibited in all cases.

(C) Toxicity

When given in drinking water (2%) or injected i.p. (200 mg/kg twice a day) MFMDP induced the following toxic effects observed after 10 days of treatment:

25% decrease in body weight
30–40% decrease in water intake
50% drop in blood leukocytes
15% animals dead after 10 days.

The LD50 is acute i.p. injection was between 1 and 3 g/kg in mice.

What is claimed is:

1. A compound of the formula:

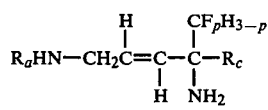

wherein

R$_a$ is hydrogen or L-δ-glutamyl,

R$_c$ is hydrogen or —COR$_3$ wherein R$_3$ is hydroxy, or when R$_a$ is hydrogen, C$_1$–C$_8$ alkoxy, and p is 1 or 2, or a pharmaceutically acceptable addition salt thereof.

2. A compound as defined in claim 1 wherein R$_c$ is hydrogen.

3. The compound as defined in claim 2 which is 1-fluoro-2,5-diamino-3-(E)-pentene.

4. The compound as defined in claim 2 which is 1,1-difluoro-2,5-diamino-3-(E)-pentene.

5. A compound as defined in claim 1 wherein R$_c$ is —COR$_3$.

6. A compound as defined in claim 1 wherein R$_3$ is hydroxy.

7. The compound as defined in claim 6 which is 2-fluoromethyl-2,5-diamino-3-(E)-penten-1-oic acid.

8. The compound as defined in claim 6 which is 2-difluoromethyl-2,5-diamino-3-(E)-penten-1-oic acid.

9. A compound as defined in claim 1 wherein R$_3$ is C$_1$–C$_8$ alkoxy.

10. The compound as defined in claim 9 which is methyl 2-fluoromethyl-2,5-diamino-3-(E)-penten-1-oate.

11. The compound as defined in claim 9 which is methyl 2-difluoromethyl-2,5-diamino-3-(E)-penten-1-oate.

12. The compound as defined in claim 9 which is ethyl 2-fluoromethyl-2,5-diamino-3-(E)-penten-1-oate.

13. The compound as defined in claim 9 which is ethyl 2-difluoromethyl-2,5-diamino-3-(E)-penten-1-oate.

14. A compound as defined in claim 9 wherein R$_a$ is hydrogen.

* * * * *

UNITED STATES PATENT AND TRADEMARK OFFICE
CERTIFICATE OF CORRECTION

PATENT NO. : 4,439,619
DATED : March 27, 1984
INVENTOR(S) : Philippe Bey, Fritz Gerhart and Michel Jung      Page 1 of 4

It is certified that error appears in the above-identified patent and that said Letters Patent is hereby corrected as shown below:

At Column 13, lines 5-10, Formula VIII, the patent reads:

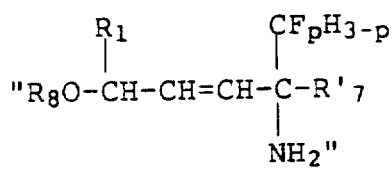

and should read:

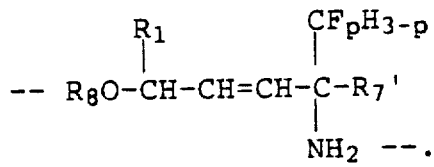

At Column 14, lines 21-28, Formula XIII, the patent reads:

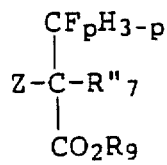

and should read:

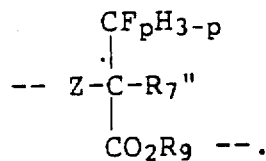

UNITED STATES PATENT AND TRADEMARK OFFICE
CERTIFICATE OF CORRECTION

PATENT NO. : 4,439,619

DATED : March 27, 1984

INVENTOR(S) : Philippe Bey, Fritz Gerhart and Michel Jung

It is certified that error appears in the above-identified patent and that said Letters Patent is hereby corrected as shown below:

At Column 14, lines 56-61, Formula XIV, the patent reads:

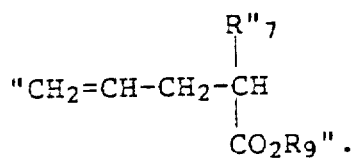

and should read:

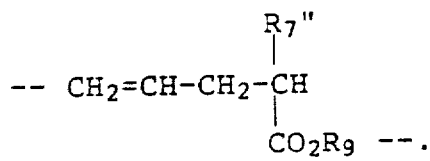

At Column 16, lines 1-5, Formula XX, the patent reads:

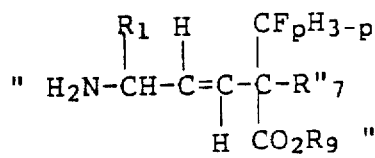

and should read:

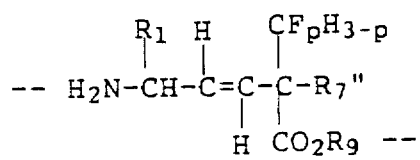

UNITED STATES PATENT AND TRADEMARK OFFICE
CERTIFICATE OF CORRECTION

PATENT NO. : 4,439,619
DATED : March 27, 1984
INVENTOR(S) : Philippe Bey, Fritz Gerhart and Michel Jung It is certified that error appears in the above-identified patent and that said Letters Patent is hereby corrected as shown below:

At Column 21, lines 50-55, in the Formula, the patent reads:

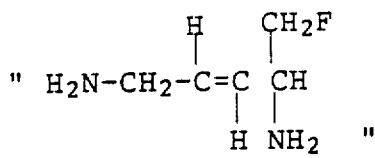

and should read:

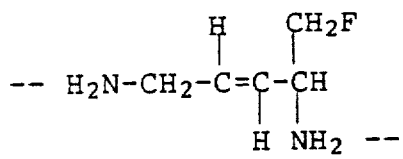

At Column 23, line 29, the patent reads "1-Fluoro-2,3-", and should read -- 1-Fluoro-2,5- --.

At Column 28, line 30, the patent reads "couling)," and should read -- coupling), --.

At Column 30, line 30, the patent reads "center of part of ABX," and should read -- center of A part of ABX, --.

UNITED STATES PATENT AND TRADEMARK OFFICE
CERTIFICATE OF CORRECTION

PATENT NO. : 4,439,619
DATED : March 27, 1984
INVENTOR(S) : Philippe Bey, Fritz Gerhart and Michel Jung It is certified that error appears in the above-identified patent and that said Letters Patent is hereby corrected as shown below:

At Column 35, lines 42-46, the patent reads:

|  | ODC Activity | | (% Control) Thymus | |
| --- | --- | --- | --- | --- |
| Inhibitors | Ventral I.P. | Prostate Gavage | I.P. | Gavage | and should read:

|  | ODC Activity | | (% Control) | |
| --- | --- | --- | --- | --- |
|  |  |  | Thymus | |
| Inhibitors | Ventral I.P. | Prostate Gavage | I.P. | Gavage |

Signed and Sealed this

Twentieth Day of March, 1990

Attest:

JEFFREY M. SAMUELS

*Attesting Officer*     *Acting Commissioner of Patents and Trademarks*